(12) United States Patent
Kiani et al.

(10) Patent No.: US 11,103,168 B2
(45) Date of Patent: Aug. 31, 2021

(54) SYSTEMS AND METHODS FOR IN VIVO DETECTION OF ELECTROPHYSIOLOGICAL AND ELECTROCHEMICAL SIGNALS

(71) Applicant: NEW YORK UNIVERSITY, New York, NY (US)

(72) Inventors: Roozbeh Kiani, New York, NY (US); Davood Shahrjerdi, New York, NY (US); Bayan Nasri, Brooklyn, NY (US)

(73) Assignee: NEW YORK UNIVERSITY, New York, NY (US)

( * ) Notice: Subject to any disclaimer, the term of this patent is extended or adjusted under 35 U.S.C. 154(b) by 886 days.

(21) Appl. No.: 15/671,648

(22) Filed: Aug. 8, 2017

(65) Prior Publication Data

US 2018/0035934 A1    Feb. 8, 2018

Related U.S. Application Data

(60) Provisional application No. 62/372,099, filed on Aug. 8, 2016.

(51) Int. Cl.
*A61B 5/1473* (2006.01)
*H01L 21/306* (2006.01)
(Continued)

(52) U.S. Cl.
CPC ........ *A61B 5/14735* (2013.01); *A61B 5/0004* (2013.01); *A61B 5/0022* (2013.01); *A61B 5/7203* (2013.01); *A61B 5/725* (2013.01); *G01N 27/4146* (2013.01); *H01L 21/02425* (2013.01); *H01L 21/02527* (2013.01);
(Continued)

(58) Field of Classification Search
None
See application file for complete search history.

(56) References Cited

U.S. PATENT DOCUMENTS

| 5,580,802 A * | 12/1996 | Mayer | H01L 29/42392 |
| | | | 148/DIG. 12 |
| 2007/0034971 A1 * | 2/2007 | Anderson | H01L 27/1211 |
| | | | 257/401 |

(Continued)

*Primary Examiner* — Michael R Bloch
(74) *Attorney, Agent, or Firm* — Scully, Scott, Murphy & Presser, P.C

(57) ABSTRACT

Systems and methods for measuring electrophysiological and electrochemical signals in a portion of a body of a subject are provided. The structure includes an array of electrochemical sensors made of miniaturized multi-layer graphene, an array of electrophysiological electrodes, an integrated front-end readout circuit, and narrow silicon shafts with metal spines. The sensor arrays offer significantly higher sensitivity than conventional methods and enable simultaneous, multi-site measurement of chemical and electrophysiological. The front-end circuit contains features that allow significant improvement in detection of the resulting electrochemical current produced by the electrochemical sensing electrodes. The silicone probes allow measurements deep in the body. In one example, neuroprobes are provided that include an electrophysiological sensor and an amperometric or voltammetric electrochemical sensor for detecting electrochemical signals from neuromodulators such as dopamine in a portion of a brain of a subject.

10 Claims, 17 Drawing Sheets

(51) Int. Cl.

| | | |
|---|---|---|
| *H01L 21/84* | (2006.01) | |
| *H01L 27/12* | (2006.01) | |
| *H01L 29/45* | (2006.01) | |
| *H01L 29/06* | (2006.01) | |
| *H01L 21/02* | (2006.01) | |
| *H01L 21/683* | (2006.01) | |
| *H01L 21/764* | (2006.01) | |
| *H01L 21/78* | (2006.01) | |
| *A61B 5/00* | (2006.01) | |
| *G01N 27/414* | (2006.01) | |
| *H01L 27/13* | (2006.01) | |
| *H01L 29/16* | (2006.01) | |

(52) U.S. Cl.
CPC .. *H01L 21/02664* (2013.01); *H01L 21/30604* (2013.01); *H01L 21/6835* (2013.01); *H01L 21/764* (2013.01); *H01L 21/78* (2013.01); *H01L 21/84* (2013.01); *H01L 27/1203* (2013.01); *H01L 27/13* (2013.01); *H01L 29/0649* (2013.01); *H01L 29/456* (2013.01); *A61B 2562/0285* (2013.01); *A61B 2562/046* (2013.01); *A61B 2562/125* (2013.01); *H01L 29/0676* (2013.01); *H01L 29/1606* (2013.01); *H01L 2221/68354* (2013.01); *H01L 2221/68368* (2013.01); *H01L 2221/68381* (2013.01)

(56) References Cited

U.S. PATENT DOCUMENTS

| | | | |
|---|---|---|---|
| 2013/0018599 A1* | 1/2013 | Peng | H01L 29/778 |
| | | | 702/30 |
| 2015/0330941 A1* | 11/2015 | Smith | H01L 27/1218 |
| | | | 257/253 |
| 2017/0181669 A1* | 6/2017 | Lin | A61B 5/145 |

* cited by examiner

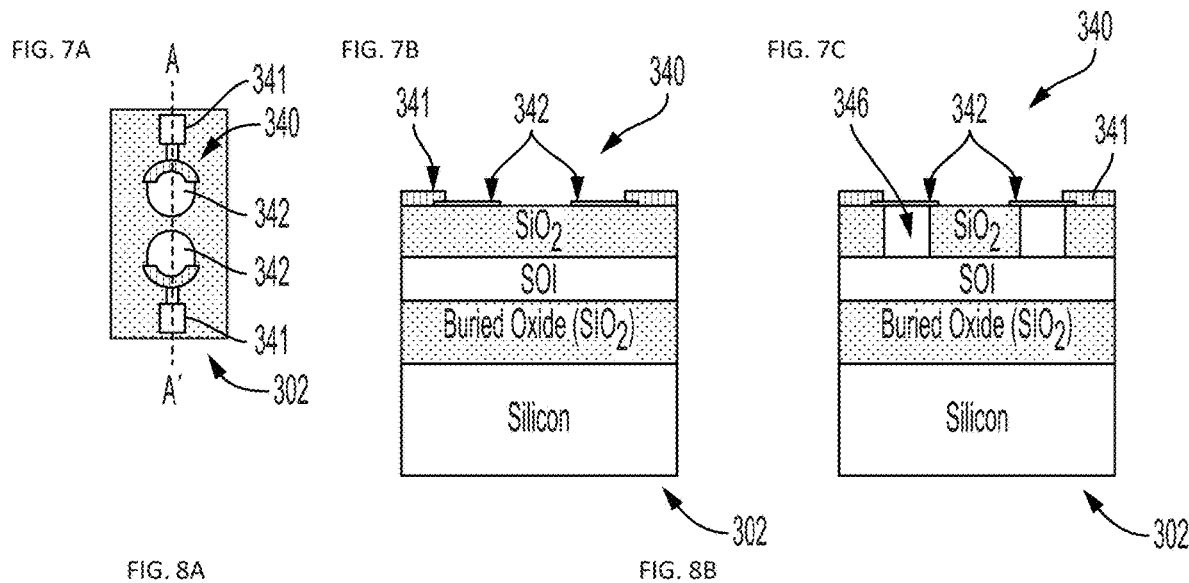

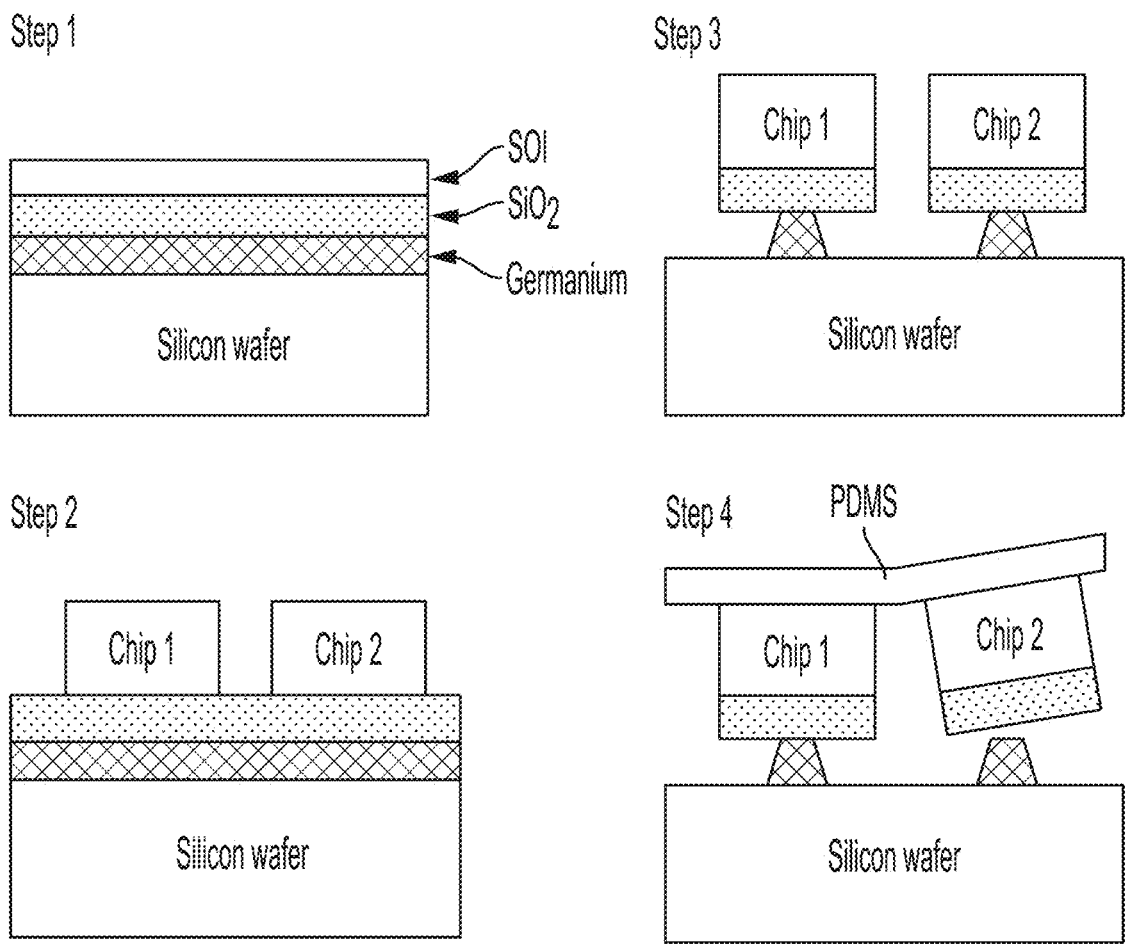

SYSTEMS AND METHODS FOR IN VIVO DETECTION OF ELECTROPHYSIOLOGICAL AND ELECTROCHEMICAL SIGNALS

CROSS REFERENCE TO RELATED APPLICATION

The present invention claims the benefit of U.S. Provisional Patent Application No. 62/372,099 filed Aug. 8, 2016, the entire content and disclosure of which is incorporated herein by reference.

TECHNICAL FIELD

The present disclosure relates generally to systems and methods for detecting electrophysiological and chemical signals in a portion of a body of a subject.

BACKGROUND

Complex computations in the brain are implemented by networks of neurons that communicate via electrical action potentials and chemical neuromodulators. A complete understanding of neural computations require simultaneous measurement of those electrical and chemical signals. However, neuroscientists usually rely on the measurement of either electrophysiological activity or chemical signals at any given time. Generally, the detection devices for measuring electrophysiological and electrochemical signals employ passive sensors owing to their simplicity, and adequately fast and reproducible measurements. However, these devices are often bulky, capable of making only one type of measurement, and in many cases suitable for single site measurements.

SUMMARY

Embodiments described herein relate generally to systems and methods for measuring electrophysiological and electrochemical signals in a portion of a body of a subject and, in particular, to neuroprobes that include an electrophysiological sensor and an amperometric or voltammetric electrochemical sensor for detecting electrochemical signals from neurotransmitters such as dopamine in a portion of a brain of a subject.

In some embodiments, a sensor assembly comprises a probe structured to be inserted into a portion of a body of a subject. An electrochemical sensor is positioned on the probe. The electrochemical sensor comprises a planar multilayer graphene configured to receive an activating signal for redox of an analyte, such as, for example, dopamine, included in a bodily fluid present in the portion of the body in contact with a surface of the sensor, and sense an electrochemical signal produced by the redox of the analyte. The electrochemical signal is indicative of a concentration of the analyte.

In some embodiments, a sensor assembly comprises a substrate structured to be inserted into a portion of a body of a subject. A potentiometric electrochemical sensor is positioned on the substrate. The electrochemical sensor comprises a planar multilayer graphene and a field-effect transistor (FET) configured to receive an activating signal for redox of an analyte included in a bodily fluid present in the portion of the body in contact with a surface of the multilayer graphene. The electrochemical sensor is further configured to sense an electrochemical signal produced by the redox of the analyte, the electrochemical signal indicative of a concentration of the analyte.

In some embodiments, a front-end circuitry for operating a sensor assembly comprises an electrochemical signal measuring circuitry configured to provide a voltammetry scan signal to an electrochemical sensor. The voltammetry scan signal comprises a dual-slope voltage ramp configured to cause an analyte in contact with a surface of the electrochemical sensor to undergo a redox reaction such that an electrochemical signal is produced in the electrochemical sensor. The electrochemical signal includes a background current and an electrochemical (redox) current indicative of a concentration of the analyte. A background noise reduction circuitry is configured to generate a subtraction signal having an opposite polarity to the background current so as to subtract the background current from the total current signal. Moreover, an analog to digital conversion (ADC) circuitry is configured to convert the electrochemical signal that comprises an analog signal, into a digital signal.

Some embodiments relate to a method for use of a probe. In some examples, the probe can be inserted into a portion of a brain of a subject. The probe comprises an electrochemical sensor including a planar multilayered graphene. An activating signal is applied on the electrochemical sensor. The activating signal is configured to decompose the analyte included in a bodily fluid present in the portion of the body, e.g., the brain, in contact with the electrochemical sensor so as to produce an electrochemical signal indicative of the concentration of the analyte. The electrochemical signal corresponding to the concentration of the analyte in the portion of the body, e.g., brain, is measured via the electrochemical sensor, and communicated to a global controller.

In some embodiments, a sensor assembly comprises a substrate structured to be inserted into a portion of a body of a subject. An electrophysiological sensor is positioned on the substrate. The electrophysiological sensor comprises a plurality of silicon nanopillars positioned on a first location of the substrate.

Some embodiments relate to a method of forming a sensor assembly that comprises positioning a first sensor on a first location of a substrate. The first sensor comprises an electrophysiological sensor. A second sensor is positioned on a second location of the substrate. The second sensor comprises an electrochemical sensor. A first surface of the substrate is selectively etched so as to form a probe. A second surface of the substrate opposite the first surface is also selectively etched so as to define a thickness of the probe. A plurality of spines can be formed within the substrate.

Some embodiments relate to a method of forming a graphene electrochemical sensor that comprises growing graphene on a first substrate. The first substrate is immersed in a solution formulated to dissolve the first substrate. The graphene is released from the first substrate. The graphene is positioned on a second substrate comprising a silicon on insulator (SOI) layer and an insulating layer positioned on the SOI layer. The graphene is positioned on the insulating layer.

Some embodiments relate to a method that comprises growing a sacrificial layer on a base layer. An insulating layer is disposed on the sacrificial layer. An active layer is disposed on the insulating layer. A plurality of electronic chips are fabricated in the active layer. The active layer and the insulating layer are selectively etched so as to separate the plurality of electronic chips. The sacrificial layer is partially etched, the plurality of electronics chips are mechanically exfoliated from the sacrificial layer.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are, therefore, not to be considered limiting of its scope, the disclosure will be described with additional specificity and detail through use of the accompanying drawings.

FIG. 6 panel D is a normalized distribution plot showing the size variations of pores formed in a template layer within which the block co-polymer is disposed; FIG. 6 panels E-G are SEM images of various stages in fabrication of silicon nanostructures using the block co-polymer particles as an etch mask.

FIG. 7A is a top view of an electrochemical sensor according to an embodiment; FIG. 7B is side cross-section view of the electrochemical sensor of FIG. 7A along A-A of FIG. 7A; FIG. 7C is a cross-section of another embodiment the electrochemical sensor of FIG. 7A along A-A of FIG. 7A in which an air-gap is positioned beneath a sensing layer of the electrochemical sensor.

FIG. 8A is a SEM image of a multilayer graphene electrode including a graphene disc; FIG. 8B is an optical image of a multilayer graphene electrode including a graphene nanoribbon; FIG. 8C is a plot of total current vs voltage; FIG. 8D is a plot of electrochemical current corresponding to 1.5 micromolar dopamine detected in vitro via fast scan cyclic voltammetry (FSCV) using the graphene disc electrode of FIG. 8A.

FIG. 13 is a schematic illustration of a process for fabricating a plurality of chips on a substrate and separating individual chips from the substrate.

Figure 1:
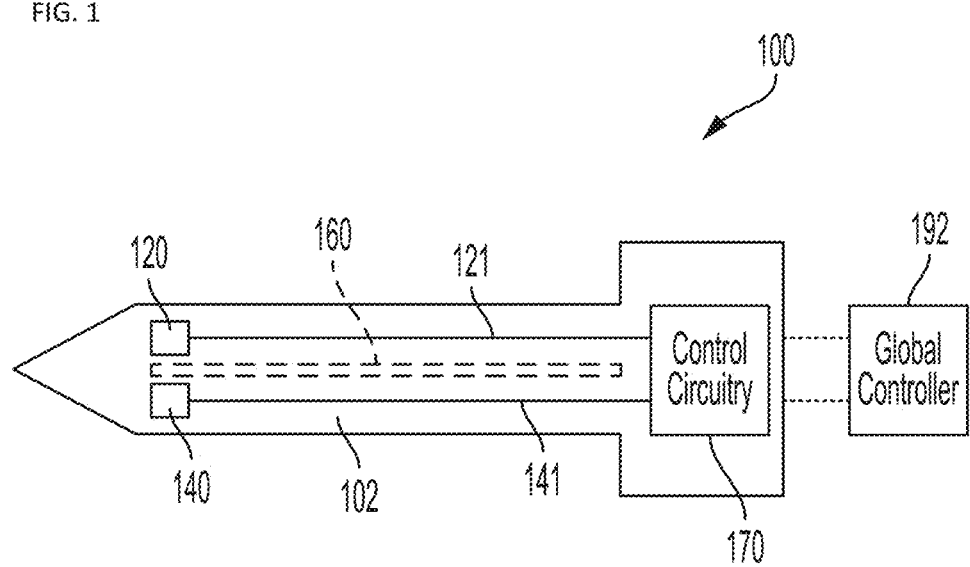
FIG. 1 is schematic illustration of a sensor assembly for simultaneous measurement of electrophysiological and electrochemical signals in a portion of a human body, according to an embodiment.
Figure 15:
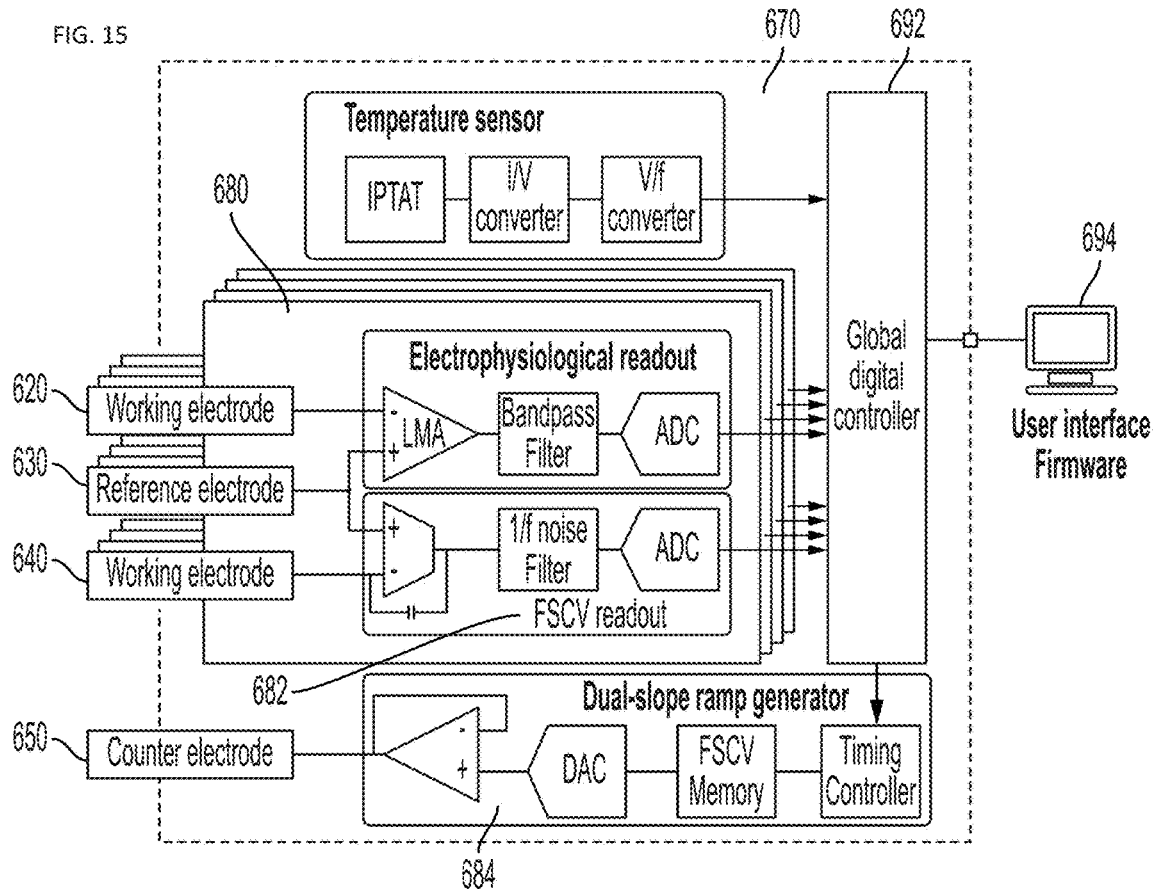
FIG. 15 is a schematic block diagram of an integrated sensor platform including a front-end circuitry which is coupled to a user interface via a global controller.

2, the global controller of FIG. 1 or FIG. 15, the user interface of FIG. 15 or any other controller described herein.

Reference is made to the accompanying drawings throughout the following detailed description. In the drawings, similar symbols typically identify similar components unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures can be arranged, substituted, combined, and designed in a wide variety of different configurations, all of which are explicitly contemplated and made part of this disclosure.

DETAILED DESCRIPTION OF VARIOUS EMBODIMENTS

Embodiments described herein relate generally to systems and methods for detecting electrophysiological and chemical signals in a portion of a body of a subject and, in particular, to neuroprobes that include an electrophysiological sensor and an amperometric or voltammetric electrochemical sensor for measuring chemical signals from neurotransmitters such as dopamine in a portion of a brain of a subject. Various embodiments of the systems and methods of fabricating neuroprobes and for measuring electrophysiological and electrochemical signals described herein provide benefits including, for example: allowing multisite measurements of dopamine and electrical signals simultaneously with high spatio temporal resolution and allowing simultaneous recording of various neurotransmitters such as dopamine, serotonin, acetylcholine, glutamate, glucose, and potentially other chemicals, along with action potentials and local field potentials.

Described herein are several features of neuroprobe fabrication, structure and function, including (1) providing structural spines in a substrate of the neuroprobe so as to increase mechanical strength and rigidity; (2) providing autonomous, low-power silicon integrated front-end circuitry to enhance the detection limit of in-vivo or in-vitro sensors for electrochemical and electrophysiological measurements (3) providing miniaturized highly-selective silicon or platinum silicide nanostructure electrodes for improved neural recording; (4) providing multilayer miniaturized graphene and/or silicon or platinum silicide nanostructure electrodes for simultaneous measurements of neurotransmitters such as dopamine and neural recording of electrophysiological signals. One or more of these features may be combined in a single system or method.

Sensor Assembly Summary

FIG. 1 is a schematic illustration of a sensor assembly 100 for simultaneous measurement of electrophysiological and chemical signals in a portion of a body of a subject. For example, the sensor assembly 100 includes a neuroprobe configured to simultaneously measure action potentials and neurotransmitters (e.g., dopamine, serotonin, etc.) in a portion of a brain of a subject. The sensor assembly 100 includes a substrate or probe 102, a first sensor 120, a second sensor 140 and optionally a front-end circuitry 170.

The substrate or probe 102 is structured to be inserted into a portion of a body of a subject, for example, a portion of a brain of a subject. The substrate 102 is formed from any suitable material, for example, silicon, oxides, metals, polymers, etc. In some embodiments, the substrate 102 contains an insulating layer (e.g., silicon oxide or silicon nitride). In some embodiments, the substrate 102 includes a base layer (e.g., base silicon layer), a first insulating layer (e.g., a first silicon oxide layer) positioned on the base layer, an active layer positioned on the first insulating layer (e.g., an n-type or p-type silicon layer) and a second insulating layer (e.g., a second silicon oxide layer) positioned on the active layer. In particular embodiments, for example shown in FIGS. 3A-C, the substrate 102 includes a silicon on insulator (SOI), which is shaped in the form of a probe such that the substrate 102 can be inserted into the portion of the body (e.g., the brain) of the subject. The SOI substrate includes a thin silicon layer positioned between a buried oxide layer and a top silicon oxide layer.

With continued reference to FIG. 1, the first sensor 120 is positioned at a first location on the substrate 102. The first sensor 120 is configured to measure electrophysiological signals in the portion of the body (e.g., the brain) of the subject. For example, the first sensor 120 is configured to measure action potentials and/or local field potentials in a portion of the brain of a subject. While FIG. 1 shows the sensor assembly 100 including a single first sensor 120, in some embodiments, the sensor assembly 100 may include an array of first sensors 120 positioned on the substrate 102.

The first sensor 120 is made of a highly conducting and biocompatible material, for example bio-compatible metals, conducting polymers, carbon, graphene, carbon nanotubes (CNT), etc. The first sensor 120 may be monolithically integrated with the substrate 102 or a separate component attached thereto. A metal interconnect line 121 is positioned on the substrate 102. The metal interconnect line 121 is electrically connected to the first sensor 120 so as to provide electrical communication therewith, for example, with the front-end circuitry 170. The first sensor 120 may include micro and/or nanostructures positioned thereon, for example, to increase a surface area of the first sensor 120. For example, the first sensor 120 may include microporous platinum, an array of CNTs, metallic nanoparticles, nanopyramids, nanopillars, nanopores, silicon nanopillars or any other suitable micro or nanostructures positioned thereon.

The second sensor 140 is positioned at a second location of the substrate 102 which is different than the first location at which the first sensor 120 is located. The second sensor 140 is configured to measure chemical signals in the portion of the brain. For example, the second sensor 140 may be configured to electrochemically measure dopamine, serotonin, acetylcholine, glutamate, glucose or any other neurotransmitters in the portion of the brain. While FIG. 1 shows the sensor assembly 100 including a single second sensor 140, in various embodiments, the sensor assembly 100 includes a plurality of second sensors 140. The second sensor 140 may include a sensing layer formed from any suitable conductive material suitable for detecting a target chemical (e.g., a neurotransmitter such as dopamine, serotonin, acetyl choline, etc.), for example, metals, conducting polymers, CNTs, graphene etc. In particular embodiments, the sensing layer includes a planar multilayer such as a continuous graphene electrode (e.g., a graphene disc or block) or an assembly of patterned graphene ribbons (e.g., graphene nanoribbons having space there between of 20 nm to 40 μm). The sensing layer may be formed separately, and then positioned on the substrate 102 using any suitable pick-and-place method. In some embodiments, a cavity is defined in the substrate 102 below the sensing layer so as to form an air gap that increases the effective surface area of the planar multilayer graphene electrode. The air gap reduces the flicker noise at the interface of the sensing layer and the substrate 102 (e.g., an oxide layer included in the substrate 102). In another embodiment, the multilayer graphene electrode 140 is directly placed on a hexagonal boron nitride insulating layer to help reduce the low-frequency noise. The boron nitride layer is in contact with either the insulating $SiO_2$ or $SiN_x$ or the silicon base layer.

In some embodiments, with continued reference generally to FIG. 1, the second sensor 140 includes an amperometric (i.e., a current sensing) sensor. In such embodiments, the sensor assembly 100 also includes a metal interconnect line 141 positioned on the substrate 102. The metal line 141 is electrically connected to the second sensor 140 so as to provide electrical communication therewith, for example, with the front-end circuitry 170. A reference electrode (not shown) may also be positioned on the substrate 102 so as to provide an electrical reference.

In some embodiments, a counter electrode (not shown) is also positioned on the substrate 102 (e.g., a platinum, carbon, CNT or a graphene counter electrode). The counter electrode provides a path for electrons generated on the surface of the second sensor 140 due to electrochemical redox reaction of a target chemical (e.g., dopamine) in the presence of an electrolyte (e.g., the cerebrospinal fluid present in the portion of the brain into which the sensor assembly 100 is inserted) to be returned back to the electrolyte.

With continued reference to FIG. 1, the front-end circuitry 170 is electrically coupled to each of the first sensor 120 and the second sensor 140, for example, via the first electrode (i.e., first interconnect metal lines 121) and the second electrode (i.e., second interconnect metal lines 141). The front-end circuitry 170 is configured to control the operation of each of the first sensor 120 and the second sensor 140, detect chemical signals therefrom, and/or filter noise. The front-end circuitry 170 may be electrically coupled to a global controller 192: for example, a multiplexer, a computing device (e.g., the computing device 2030), or any other suitable global controller. The control circuitry 170 may also be positioned on the substrate 102. For example, the front-end circuitry 170 may include a very large scale integrate (VLSI) circuit fabricated on an active layer of the substrate 102 or positioned thereon. In some embodiments, each of the first sensor 120, the second sensor 140, and/or the front-end circuitry 170 are formed on a sensor chip separately from the substrate 102. One or more sensor chips are positioned on the substrate 102 so as to form the sensor assembly 100. The front-end circuitry 170 may be incorporated on the substrate or probe 102 or be separate therefrom. It should be appreciated that while the front-end circuitry 170 is described with respect to the sensor assembly 100, the front-end circuitry 170 may be used independently to control the operation of any electrochemical and/or electrophysiological sensor. For example, the front-end circuitry 170 may be used to control the operation of any suitable biochemical, biological, environmental, or any other electrochemical sensor configured to determine a concentration of any suitable analyte.

The sensor assembly 100 or any other sensor assemblies described herein may be used to simultaneously measure electrophysiological signals (e.g., action potentials and/or local field potentials) and electrochemical signals (e.g., corresponding to concentration of dopamine, serotonin, acetylcholine, glutamate, glucose, etc.) in a portion of a brain of subject, or any other portion of a body of a subject with high spatio-temporal resolution. In this manner, a holistic picture of brain activity of the subject can be determined as it plans actions or responds to various visual, tactile, olfactory, auditory, or gustatory stimuli.

Figure 21:
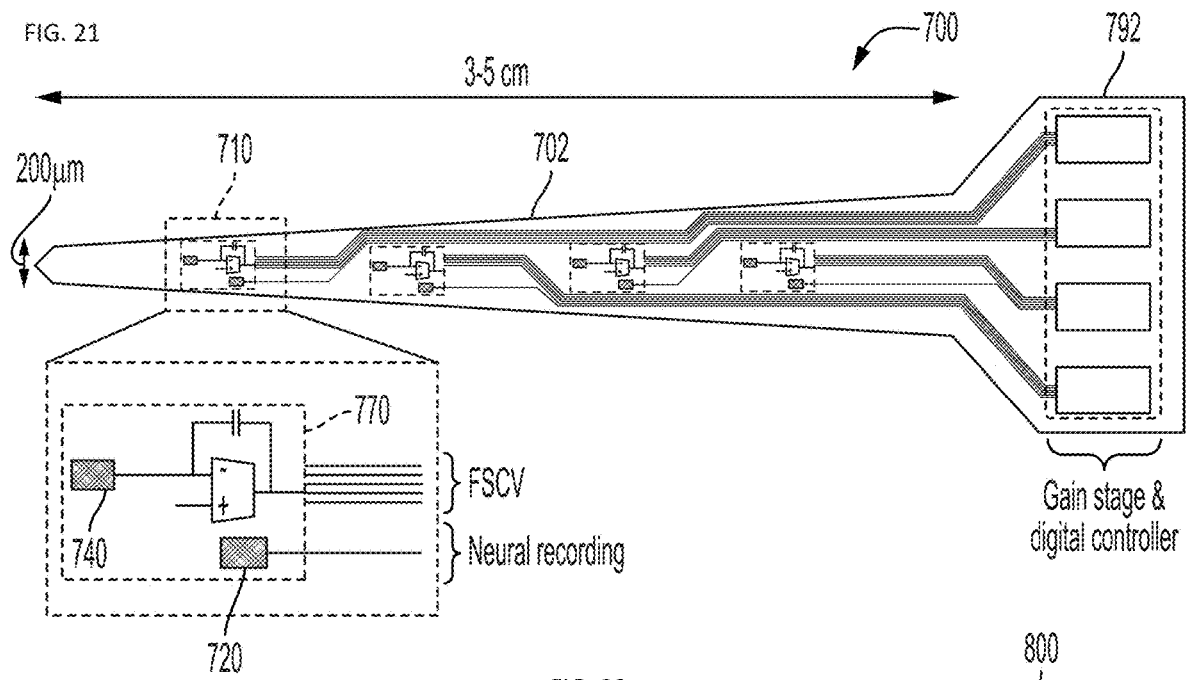
FIG. 21 is a top view of a sensor assembly according to another embodiments; inset is a schematic circuit diagram of a single chip of the sensor assembly.

FIG. 21 shows another embodiment of a sensor assembly 700. The sensor assembly 700 includes a substrate 702 which may be substantially similar to the substrate 102/202/320/402 or any other substrate described herein. A plurality of sensor chips 710 are positioned on the substrate 702. Each of the plurality of sensor chips 710 includes a first sensor 720 for electrophysiological measurements, a second sensor 740 for electrochemical measurements, and a front-end circuitry 770. The first sensor 720 may be substantially similar to the first sensor 120/220/320 or any other first sensor described herein. The second sensor 740 may be substantially similar to the second sensor 140/240/340/440/540/640 or any other second sensor described herein. Furthermore, the front-end circuitry 770 may be substantially similar to front-end circuitry 170/670 or any other front-end circuitry described herein. A global controller 792 configured to provide signal gain, noise filtering, and/or multiplexing may also be integrated on the substrate 702.

Probe/Substrate

As discussed above, FIG. 1 illustrates a system comprising a probe 102. In the illustrated embodiment, a plurality of spines 160 is positioned within the probe/substrate 102 so as to provide mechanical strength to the substrate. For example, a plurality of channels is defined on a back side of the substrate (e.g., via deep reactive ion etching (DRIE)). The plurality of channels is filled with a pliable metal (e.g., gold, silver, platinum, copper, aluminum, etc.) so as to form metallic spines therein. The metal may be deposited using any suitable process, for example, sputtering, electron beam evaporation, thermal evaporation, electroplating, etc. The plurality of spines 160 provide mechanical strength to substrate 102 while retaining flexibility of the substrate 102 such that the substrate can be inserted into the portion of the body of the subject with minimal risk of breaking of the substrate 102.

Figure 3A:
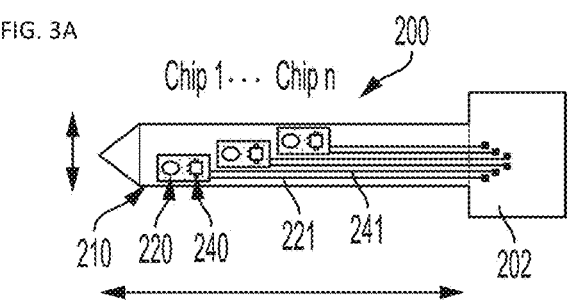
FIG. 3A is a top view of a sensor assembly according to another embodiment.
Figure 3B:
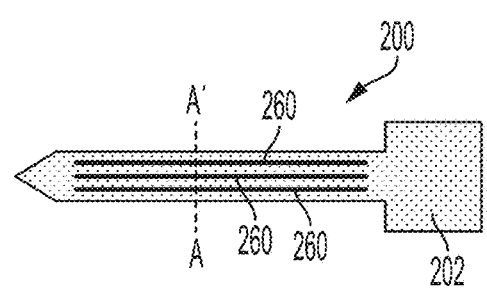
FIG. 3B is a bottom view.
Figure 3C:
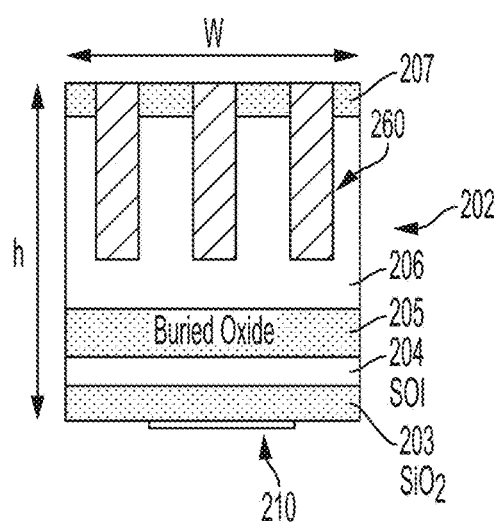
FIG. 3C is a side cross-section view of the sensor assembly of FIG. 3A along the line A-A shown in FIG. 3B.

FIGS. 3A-C show various views of another embodiment of a sensor assembly 200 for simultaneous measurement of electrophysiological and chemical signals in a portion of a brain of a subject. The sensor assembly 200 includes a neuroprobe configured to simultaneously measure action potentials and concentration of neurotransmitters (e.g., dopamine, serotonin, acetyl choline, glutamate, glucose, etc.) in the portion of the brain of the subject. The sensor assembly 200 includes a substrate 202 and a plurality of sensor chips 210 including a first sensor 220 and a second sensor 240 positioned on the substrate 202. The sensor assembly 200 is be configured to penetrate into the tissue (e.g., a portion of a brain of the subject) to perform electrophysiological and chemical recordings from various brain structures at different depths relative to the brain surface.

The substrate 202 is structured to be inserted into a portion of a body of a subject, for example, the portion of the brain of the subject and is shaped to form a probe. In some embodiments, the substrate 202 forming the probe has a length in the range of 10-20 mm, a width of less than 300 microns and a thickness of less than 300 microns, inclusive of all ranges and values there between. A tip of the substrate 202 may be shaped to have a sharp tip so as to facilitate penetration into the tissue (e.g., the brain) of the subject. FIG. 3C shows a side cross-section view of the sensor assembly 200 in an upside down position. The substrate 202 includes an active layer 204 including an SOI. The active layer 204 is interposed between a first insulating layer 205 which includes a BOX layer, and a second insulating layer 203 which includes a silicon oxide layer. The first insulating layer 205 is positioned on a first surface of a base layer 206, for example, a bulk silicon base layer. The plurality of chips 210 are positioned on the second insulating layer 203. A third insulating layer 207 is positioned on a second surface of the base layer 206 opposite the first surface. The third insulating layer 207 is made of a suitable insulating material or materials, such as, but not limited to, a silicon oxide layer, a silicon nitride layer, or an aluminum oxide layer.

The brittle nature of narrow and long silicon shafts or probes makes them prone to breakage once the probes are pushed into the brain. This is due to the high bending and torsional load on the probe. The plurality of spines 260 are positioned within the substrate 202 as shown in FIGS. 3B and 3C. The plurality of spines 260 are structured to provide mechanical strength to the substrate 202. To address this, transverse trenches stretching along a longitudinal axis of the substrate may be defined on backside (i.e., the second surface) of the silicon substrate (e.g., using DRIE). The plurality of channels may be filled with a pliable metal (e.g., gold, platinum, copper, aluminum, etc.) so as to form the plurality of spines 260 therein. The metal may be deposited using any suitable process, for example, sputtering, electron beam evaporation, thermal evaporation, electroplating, etc. The plurality of spines 260 provide mechanical strength to the substrate 202 while retaining the flexibility of the substrate 202. Thus, when the substrate 202 is inserted into the portion of the body of the subject there is a minimal risk of breaking of the substrate 202.

Figure 4A:
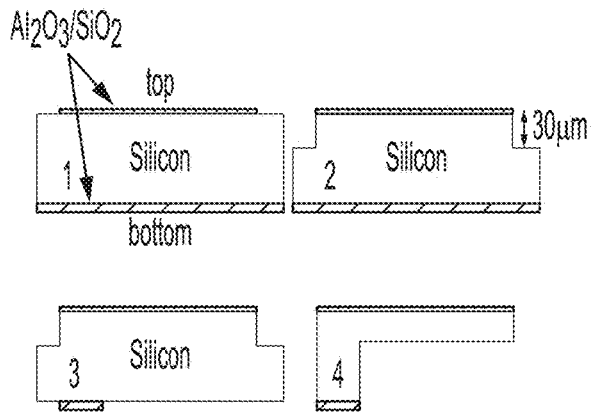
FIG. 4A is a schematic illustration of an example process of forming a substrate of a sensor assembly.
Figure 4B:
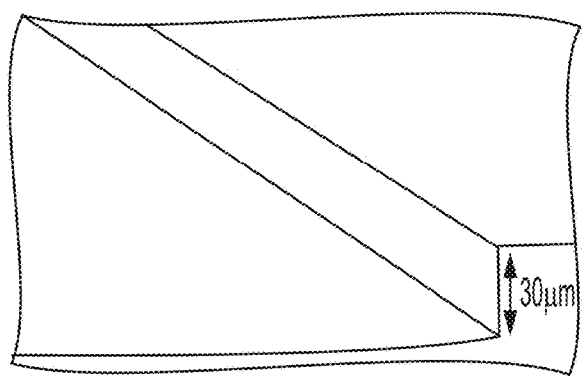
FIG. 4B is a scanning electron microscopy (SEM) image of a trench made in a silicon layer so as to form the substrate.

The substrate 202 may be formed into the shape of a neuroprobe using any suitable method. For example, FIG. 4A illustrates one embodiment of such a method used to shape a silicon substrate into a probe for insertion into a tissue of a subject. In step 1, aluminum oxide ($Al_2O_3$) and silicon oxide ($SiO_2$) are deposited on a first surface of a bulk silicon or SOI substrate, as previously described herein. An initial thickness of the substrate is in the range of 300 microns to 1 mm, inclusive of all ranges and values there between. In step 2, a first surface of the silicon substrate is etched down (e.g., using DRIE) by about 30 microns or any other suitable depth that determines the thickness of the probe formed by the substrate. In step 3, backside alignment is performed, and in step 4, a second surface of the silicon opposite the first surface is etched from the backside (i.e., the second surface), for example, using a Xenon Difluroide ($XeF_2$) or any other suitable process by about 300 to 400 microns (e.g., 310, 320, 330, 340, 350, 360, 370, 380, 390 or 400 microns) or any other suitable depth so as to release the probe. FIG. 4B shows a cross-sectional SEM image of a 30 micron deep trench formed in a silicon substrate using DRIE. In some embodiments, a laser cut process is used to produce narrow (e.g., less than 300 μm) and long (e.g., longer than 50 mm) silicon neural probes that can penetrate brain tissue for electrophysiological recordings from various brain structures at different depths relative to the brain surface.

Sensors

As discussed with regard to FIG. 1 previously, the probe 102 includes a first sensor 120 and a second sensor 140. Referring again to FIGS. 3A-C, each of the plurality of chips 210 includes the first sensor 220 and the second sensor 240. The first sensor 220 is configured to measure electrophysiological signals (e.g., action potentials and/or local field potentials) in a portion of a body of a subject (e.g., a portion of the brain of the subject). The second sensor 240 may be configured to measure chemical signals (e.g., dopamine, serotonin, acetyl choline, glutamate, glucose, etc.) in the portion of the brain of the subject. In various embodiments, each of the sensor chips 210 also include front-end circuitry (e.g., the front-end circuitry 170) positioned thereon. In some embodiments, the first sensor 220 is fabricated directly on the substrate 202 (e.g., an SOI substrate) and not included in the sensor chips 210. In such embodiments, the sensor chips 210 only include the second sensor 240 and/or the control circuitry (e.g., the control circuitry 170).

First Sensor

In particular embodiments, the first sensor 220 includes a plurality of silicon nanopillars or platinum silicide ($PtSi_2$) nanopillars (e.g., spikes, particles, peaks, poles, etc.). Generally, electrophysiology techniques employ platinum, tungsten or stainless steel wires to record from and/or stimulate neural cells. The impedance of these sensors is typically in the range of 100 kOhms-10 MOhms (measured at a frequency of 1 kHz), suitable for measurement of extracellular potentials on the microvolt scale, which is sufficient to distinguish individual action potentials. In general, decreasing the sensor area benefits the maximum selectivity of the sensor. However, the charge transfer capability of the sensor is diminished as the size of the sensor is reduced because of the increase of the sensor impendence. The thickness of such sensors is typically on the order of a few micrometers, which is not compatible with thin film microfabrication deposition techniques. They also have high cost, and the intrinsic residual stress of such thick metallic electrophysiological sensors may make them unsuitable for deep insertion into a portion of the brain of the subject.

In contrast, the first sensor 220 may include a plurality of silicon nanopillars, such as shown in FIGS. 6A-6G, having a height in a range of 100 nm to 500 nm inclusive such that the first sensor 220 (i.e., the electrophysiological sensor) has a surface area 5 times to 30 times greater than the surface area of an analogous planar electrophysiological sensor, which may be formed on a silicon on insulator substrate. The silicon nanopillars may be doped with n-type or p-type impurity atoms in a concentration in a range of $1 \times 10^{17}$ cm$^{-3}$ to $1 \times 10^{21}$ cm$^{-3}$. In some embodiments, the silicon nanopillars have a diameter in a range of 20 nm to 500 nm, and spacing between the silicon nanopillars in a range of 20 nm to 500 nm inclusive.

In particular embodiments, a platinum layer is deposited on the silicon nanopillars so as to form $PtSi_2$ nanostructures (e.g., $PtSi_2$ nanopillars, nanospikes, nanoparticles, etc.) that have lower resistivity than the silicon nanopillars. $PtSi_2$ nanostructures on silicon nanopillars provide a larger surface area for electrophysiological sensing relative to planar sensors. To make such structures, a thin platinum layer (e.g., having a thickness in a range of 30-500 nm) is deposited on the silicon nanopillars. The silicon nanopillars may then be annealed at an elevated temperature to convert the silicon nanopillars to the $PtSi_2$ nanopillars. In some embodiments, any unreacted platinum metal included in the platinum layer is selectively removed so as to expose the surface of the silicon of the silicon nanopillars beneath the platinum layer.

In particular embodiments, the $PtSi_2$ nanostructures comprise $PtSi_2$ nano-pillars having an average diameter in a range of about 10-20 nm (e.g., 10, 12, 14, 16, 18 and 20 nm inclusive of all ranges and values there between) and a height in the range of 100 to 300 nm (e.g., 100, 150, 200, 250 or 300 nm inclusive of all ranges and values there between.) The $PtSi_2$ nano-pillars may include conical nano-pillars having a sharp tip. Spacing between the $PtSi_2$ nanopillars may be in the range of 50 nm to 100 nm. Furthermore, a thickness of the platinum layer deposited on silicide nano-pillars for forming the $PtSi_2$ nano-pillars is in the range of 5 nm to 60 nm inclusive of all ranges and values there between. The PtSi$_2$ nano-pillars may have a resistivity of about 20 microOhm.cm and an active surface which is about 20 times greater than a corresponding planar PtSi$_2$ electrode.

Figure 5:
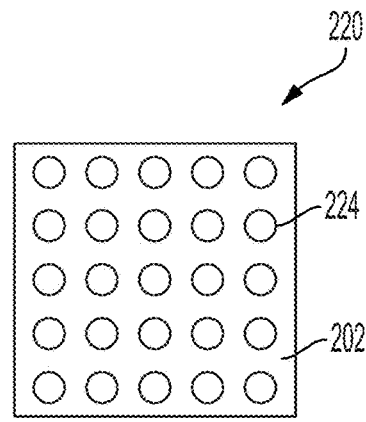
FIG. 5 is a schematic illustration of a top view of an electrophysiological sensor, according to an embodiment.
Figure 6A:
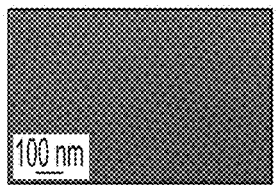
FIG. 6 panels A-C show various steps in forming of a plurality of particles of a block co-polymer on a portion of the substrate.
Figure 6B:
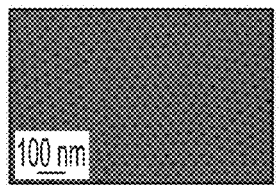
Figure 6C:
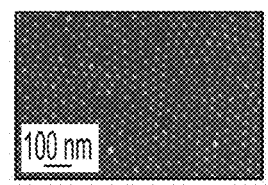
Figure 6D:
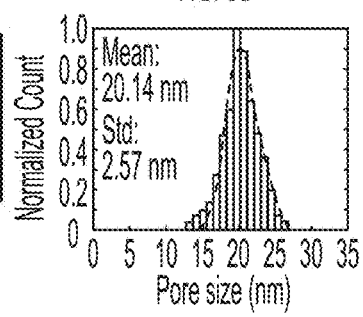
Figure 6E:
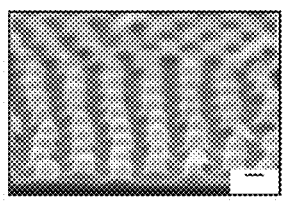
Figure 6F:
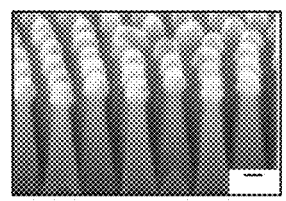
Figure 6G:
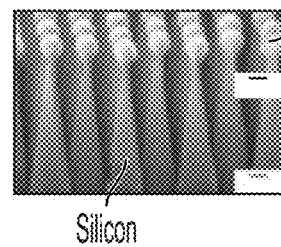

The large surface area increases the current density across the first sensor 220 thereby increasing the electrophysiological signal amplitude and/or reducing noise. For example, FIG. 5 shows a schematic illustration of the first sensor 220 according to an embodiment. The first sensor 220 includes a plurality of PtSi$_2$ nanostructures 224 fabricated on the substrate 202. The PtSi$_2$ nanostructures 224 may be fabricated using any suitable method and may have a high spatial resolution, for example, a spacing of less than 100 microns.

For example, FIG. 6 shows SEM images of a di-block copolymer used as a template for fabricating PtSi$_2$. FIG. 6 panels A-C show various steps in forming a plurality of particles of a di-block co-polymer on a portion of a silicon substrate. Unlike platinum and many other metals, silicon can be easily patterned to realize nanoscale and micron scale features thereby increasing the effective surface area of the first sensor 220. As shown in FIG. 6 panels A-C, silicon nanostructures are formed through template-assisted assembly of particles using di-block copolymer (e.g., poly(styrene-block-methyl methacrylate) [PS-PMMA])) having a pore diameter in the range of 10-20 nm on the silicon surface. The assembled nanoparticles of the di-block copolymer formed in the pores of the template serve as an etch mask for the silicon substrate. The silicon substrate is then etched (e.g., using reactive ion etching (RIE)) to a depth in the range of 100 nm to 300 nm (e.g., 120, 140, 160, 180, 200, 220, 240, 260, 280 or 300 nm inclusive of all ranges and values there between) so as to produce silicon nanostructures that are one average 200 nm tall.

FIG. 6 panel D is a normalized distribution plot showing the size of pores formed in a template layer within which the di-block copolymer is disposed. FIG. 6 panels E-G are SEM images of various stages in fabrication of silicon nanostructures using the di-block copolymer particles as an etch mask. To reduce the resistivity of the silicon and achieve uniform resistivity across the surface, platinum silicide (PtSi$_2$) is formed by depositing platinum thereon (e.g., via sputtering, electroplating, electron beam evaporation, thermal evaporation etc.), which may be followed by annealing of the platinum layer.

In some embodiments, a plurality of first electrodes 221 (FIG. 3A) are positioned on the substrate 202. A first electrode 221 of the plurality of first electrodes 221 may be electrically coupled to a corresponding first sensor 221 included in a sensor chip 210 of the plurality of sensor chips 210 so as to provide electrical communication therewith, for example, with the control circuitry 170.

Figure 9:
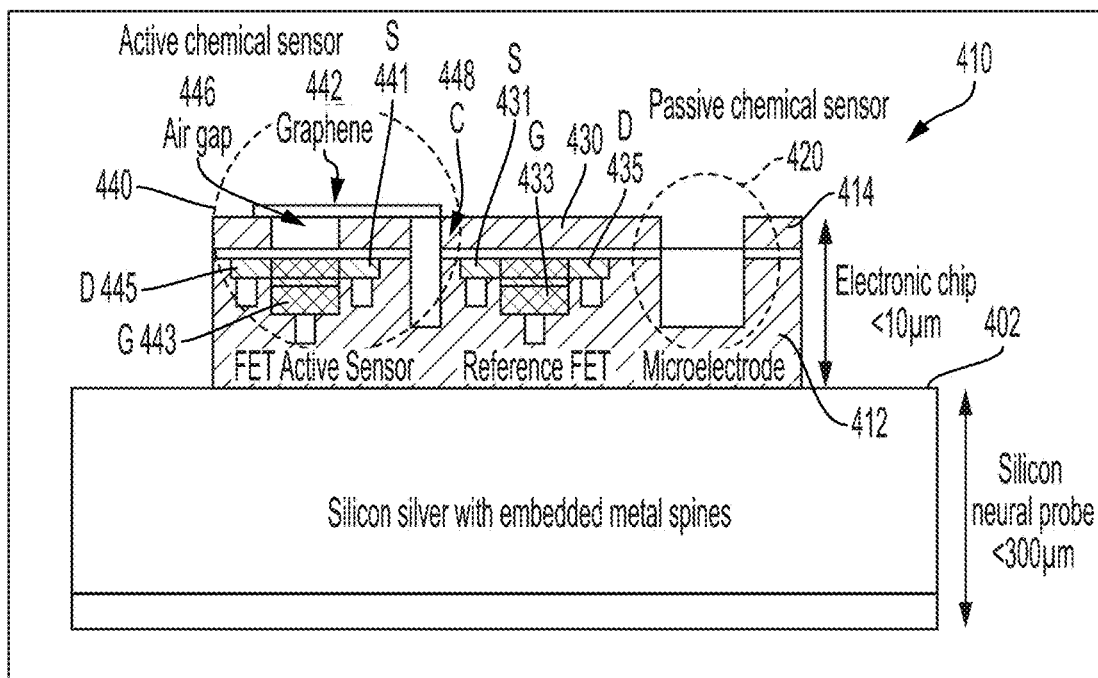
FIG. 9 is a schematic illustration of a double-gated graphene field effect transistor (FET) sensor for voltammetric detection of electrochemicals.

In some embodiments, such as shown in FIG. 9, a reference FET 430 may also be provided on the active layer 412 of the chip 410. A first sensor 420 may be positioned on the sensor chip 410. The first sensor 420 includes an electrophysiological sensor and may include any electrophysiological sensor (e.g., the first sensor 120/220) as described herein. Such an embodiment is further discussed below regarding the second sensor.

Second Sensor

As discussed previously with regard to FIG. 1, the probe 102 also includes a second sensor 140. With reference to FIGS. 3A-B, the second sensor 240 is positioned at a second location of each sensor chip 210, which is different from the first location at which the first sensor 220 is located. The second sensor 240 is configured to measure chemical signals in a portion of the brain. For example, the second sensor 240 may be configured to electrochemically measure dopamine, serotonin, acetylcholine, glutamate, glucose, or any other neurotransmitters in the portion of the brain. The second sensor 240 (i.e., the electrochemical sensor) is configured to receive an activating signal for redox of the analyte included in a bodily fluid present in the portion of the body in contact with a surface of the sensor, and sense an electrochemical signal produced by the redox of the analyte. The electrochemical signal is indicative of a concentration of the analyte.

The second sensor 240 may include a sensing layer formed from any conductive material (e.g., metals, conducting polymers, CNTs, graphene etc.) suitable for detecting a target chemical (e.g., a neurotransmitter such as dopamine, serotonin, acetyl choline, glutamate, glucose, etc.). In particular embodiments, the sensing layer includes a planar multilayer graphene, for example, a continuous graphene electrode (e.g., a graphene disc) or an assembly of patterned graphene ribbons (e.g., multilayered graphene nanoribbons). Graphene is an atomically thin layer of hexagonally bonded carbon atoms that exhibits superior electrochemical properties relative to commonly used electrodes. The multilayer graphene may be particularly beneficial for receiving a voltammetry scan signal (e.g., an FSCV signal) for sensing of dopamine or any other target analyte in the vicinity of the sensing layer of the second electrode 240 that is subjected to a cyclic potential. The resultant redox current is proportional to the analyte concentration. The use of multilayer graphene enables miniaturization, and thus the implementation of multi-electrode arrays, while the excellent electrical properties of the graphene improves the sensitivity of the second sensor 240.

The multilayer graphene sensing layer may be formed separately (e.g., via large-area epitaxial growth of mono and multilayer graphene on copper, nickel or silicon carbide substrates) and then removed by etching the substrate. The mono or multilayer graphene discs or nanoribbons may then be positioned on the chip 210 so as to form the sensing layer of the second sensor 240 using any suitable method. In some embodiments, mechanical exfoliation may be used to transfer the multilayer graphene to the chip 210. Multilayer graphene may also be obtained by stacking individual monolayers of graphene.

In some embodiments, the second sensor 140/240 may include a potentiometric sensor (i.e. a voltage measuring sensor). In such embodiments, with reference to FIG. 1, the second sensor 140 comprises an active FET defined in an active layer of the substrate 102 (e.g., a silicon layer of a SOI substrate). The active FET includes an active FET source, an active FET gate and an active FET drain defined in an active layer of the substrate 102. The active FET gate is positioned above a cavity defined in the substrate 102 below the sensing layer of the second sensor 140, such that the air gap is interposed between the active FET gate and the sensing layer. The active FET gate is made of carbon materials that are coupled to the FET through the electrolyte. A bottom gate is used to bias the FET. The second sensor 140, i.e., the electrochemical sensor which includes a planar multilayer graphene, is configured to receive an activating signal for redox of dopamine included in a bodily fluid that is present in the portion of the body and in contact with the surface of the sensor 140. In some embodiments, as further described herein, the second sensor 140 is configured to sense a chemical signal produced by the redox of dopamine which is indicative of a concentration of the dopamine.

In some embodiments, the second sensor 240 includes an amperometric sensor (i.e., a current sensing sensor). For example, FIG. 7 panel A is a top view and FIG. 7 panel B is a side cross-section view of amperometric second sensor 340, according to an embodiment. The second sensor 340 includes a multilayer graphene disc forming a graphene sensing layer 342 positioned on a SOI substrate 302 (e.g., substrate of the chip 210 on which the second sensor 240 is positioned). A second electrode 341 is also positioned on the substrate 302. The second electrode 341 is electrically coupled to the second sensor 340 so as to provide electrical communication therewith (e.g., with the front-end circuitry 170). A reference electrode (not shown) may also be positioned on the substrate 302 so as to provide an electrical reference.

In some embodiments, a cavity 346 is defined in the substrate 302 below the graphene sensing layer 342 so as to form an air gap there between, which increases an effective surface area of the graphene sensing layer 342. The minimum detection limit of dopamine, or any other biochemical, is defined, at least in part, by noise characteristics of the second sensor 340. Since the measurements are generally performed at low frequencies, flicker noise at the interface between the oxide and the graphene sensing layer 342 may become significant. The flicker noise may arise from carrier mobility fluctuation due to variations in charge carrier scattering. The silicon oxide layer included in the substrate 302 below the graphene sensing layer 342 may be etched so as to suspend the graphene sensing layer 342 (e.g., using a critical dry process), as shown in FIG. 7C, so as to form an air gap 346 between the graphene sensing layer 342 and the SOI layer included in the substrate 302. This structure may suppress the flicker noise by eliminating the oxide layer.

Referring again to FIG. 3A-C, the second sensor 240 also includes a second electrode 241 positioned on the substrate 202. The second electrode 241 is electrically coupled to the second sensor 240 so as to provide electrical communication therewith (e.g., with the control circuitry 170). A reference electrode (not shown) may also be positioned on the sensor chip 210 so as to provide an electrical reference.

In some embodiments, a counter electrode (not shown) is also positioned on the sensing chip 210 (e.g., a platinum, carbon, CNT or a graphene counter electrode). The counter electrode provides a low resistance path for the electrons generated on the surface of the second sensor 240 due to electrochemical redox reaction of a target chemical (e.g., dopamine) in the presence of an electrolyte (e.g., the cerebrospinal fluid present in the portion of the brain into which the sensor assembly 200 is inserted) to be returned to the electrolyte. Contact pads may also be fabricated on the substrate 202 to allow electrical coupling of the first sensor 220, the second sensor 240, the reference electrode and/or the counter electrode with external electronics (e.g., the global controller 192 or a computing device) for recording the electrophysiological and chemical signals. The first electrode 221, the second electrode 241 and/or any other conducting leads may be passivated with a biocompatible insulator, for example silicon oxide or a biocompatible polymer so as to prevent electrical shorts.

Figure 8E:
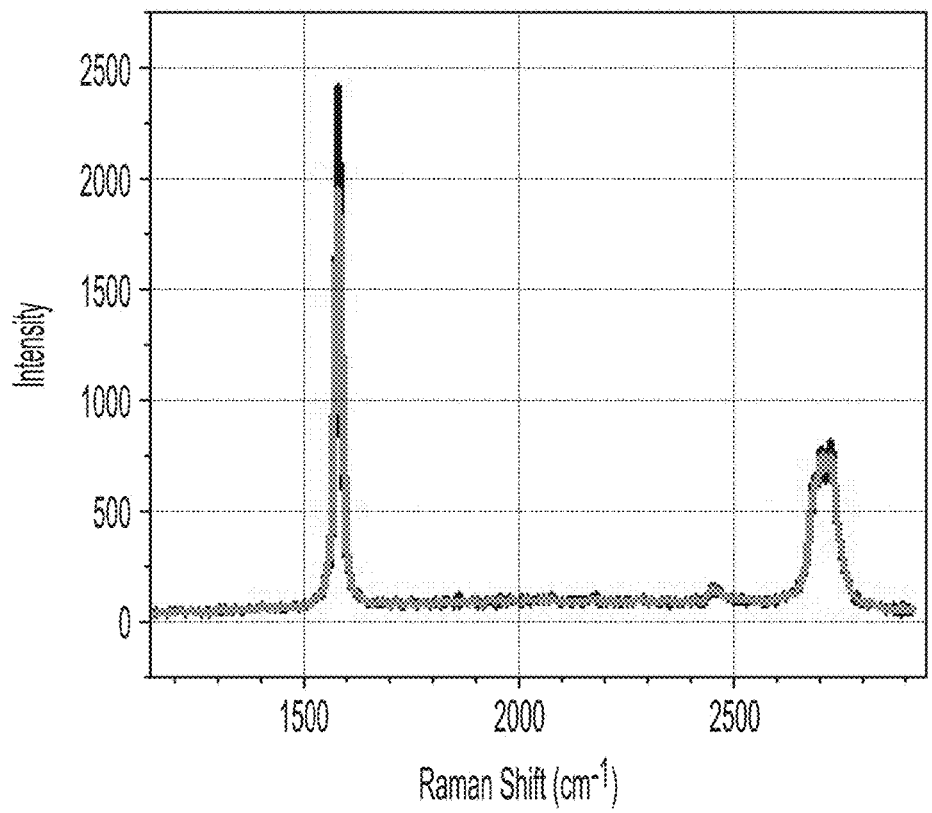
FIG. 8E is a Raman spectra of an epitaxially grown multilayer graphene film.

FIG. 8A shows an SEM image for an epitaxially grown graphene disc electrode and FIG. 8B is an SEM image of an assembly of graphene ribbon electrodes fabricated on silicon dioxide/silicon substrates that were used as sensing layers of an electrochemical sensor. The width of the graphene ribbons is within a range from 20 nm to 40 μm. These electrochemical sensors are used to perform voltammetry scan measurements on multilayer graphene electrodes for dopamine detection. As shown in FIGS. 8C and 8D, use of a multilayer graphene sensing layer allows a significant increase of the voltage ramp rate beyond the standard 400 Volts/sec that is generally used for conventional carbon fiber electrodes. Increasing the voltage ramp greatly improves voltammetry scan measurements by enhancing the sensitivity of the electrode and the temporal resolution. Voltammetry scans in FIG. 8 were performed with 200-layer graphene electrochemical sensors at 750 Volts/sec voltage ramps and no degradation of electrode performance was observed for about 104 cycles, as shown in FIG. 8C. FIG. 8E is a Raman spectra of the epitaxially grown graphene disc of FIG. 8A showing the high quality of the multilayer graphene film. In some embodiments, the voltammetry scan signals for performing redox of dopamine on the multilayer graphene electrodes are in a range of 0.1 Volts per second to 2,400 Volts per second.

Figure 8F:
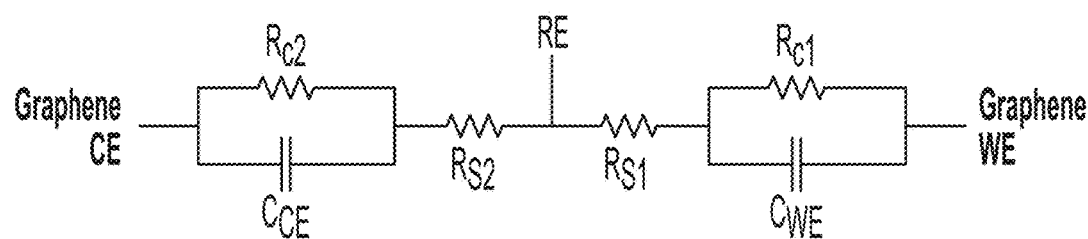
FIG. 8F is an equivalent circuit diagram of an electrochemical system including a graphene working electrode (WE) and counter electrode (CE) used to detect dopamine.

FIG. 8F is an equivalent circuit diagram of an electrochemical cell formed by the multilayer graphene working electrode (WE) (e.g., the second sensor 240/340), a counter electrode (CE) which includes, for example, a graphene counter electrode, and a reference electrode (RE), for example, a silver/silver chloride RE. Each of the graphene WE and CE is represented by a combination of the capacitance C on the surface of the WE ($C_{WE}$) and CE ($C_{CE}$) due to the formation of an electrochemical double-layer, and a resistance R of the WE ($R_{C1}$) and CE ($R_{C2}$). Furthermore, the circuit diagram of FIG. 8F also includes the resistance through the electrolyte (e.g., cerebrospinal fluid) through which the WE ($R_{S1}$), the CE ($R_{S2}$), and the RE are electrochemically coupled to each other.

For example, FIG. 9 is a schematic illustration of a side cross-section of an electrochemical active FET sensor 440 configured to electrochemically sense biochemicals (e.g., neurotransmitters such as dopamine, serotonin, acetyl choline, glutamate, glucose, etc.). The active FET sensor 440 is used as the second sensor 240 in the sensor assembly 200. The active (FET) sensor 440 is fabricated in a chip 410 positioned on a substrate 402 which in the embodiment of FIG. 9, is shaped to form a probe, as described herein. The active FET sensor 440 is defined in an active layer 412 of the chip 410 (e.g., a p-doped or n-doped silicon layer). The active FET sensor 440 includes an active FET source 441, an active FET gate 443 and an active FET drain 445 defined in the active layer 412. The active FET gate 443 is positioned below a cavity 426 defined in an insulating layer 414 (e.g., a silicon oxide layer) disposed on the active layer 412. A sensing layer 442 (e.g., a graphene disc or graphene nanoribbon) is positioned over the cavity 426 such that the cavity 426 forms an air gap interposed between the active FET gate 443 and the sensing layer 442. The sensing layer 442 provides a second gate of the active FET sensor 440.

A working electrode 448 is electrically coupled to the sensing layer 442 (e.g., the graphene disc or graphene nanoribbon). The working electrode 448 may be configured to apply a potential or a voltage to the sensing layer 442 so as to cause a redox reaction corresponding to a concentration of the target chemical (e.g., dopamine). The active FET gate 443 and the sensing layer 442 allow the active FET sensor 440 to function as a double-gated FET sensor. The electrochemical redox reaction causes a net change in the areal charge density of the sensing layer 442, thereby causing a shift in the potential of the sensing layer 442 and creating a potential difference across the cavity 446 and in the active FET gate 443. The potential difference in the active FET gate 443 causes a current to flow from the active FET source 441 to the active FET drain 445 corresponding to the potential difference across the active FET gate 443 and, thereby the concentration of the target chemical.

With continued reference to FIG. 9, a reference FET 430 may also be provided on the active layer 412 of the chip 410. The reference FET 430 includes a reference FET source 431, a reference FET drain 435, and a reference FET gate 433. The reference FET 430 may be substantially similar to the active FET sensor 440 except that it does not include the sensing layer 442 and the cavity 426. A first sensor 420 is also positioned on the sensor chip 410. The first sensor 420 includes an electrophysiological sensor and may include any electrophysiological sensor (e.g., the first sensor 120/220) as described herein.

In some embodiments, the sensing layer 442 is located on an insulator layer adjacent to a top gate electrode of the FET sensor 440. The FET sensor 440 may comprise a silicon channel interposed between a top gate dielectric and a bottom gate dielectric. A thickness of at least one of the top gate dielectric, the bottom gate dielectric, and the silicon channel thickness may be adjusted to tune an overall sensitivity of the sensor assembly. The multilayer graphene sensing layer 442 may be configured to be polarized at a constant potential so as to cause the redox reaction with dopamine. The constant potential may be applied with respect to a voltage applied to the source terminal of the FET sensor 440 such that a reference electrode may be excluded. The redox reaction of dopamine may generate excess electrons that alter the electrical characteristics of the FET sensor 440.

Expanding further, active sensors, such as field-effect transistors, offer significantly improved sensitivity due to their superior noise characteristics compared to the passive device technologies. FIG. 10 is an equivalent capacitance model of the double gated active FET sensor 440, which includes a graphene sensing layer 442. $C_{SD}$, $C_{inv}$, and $Q_0$ denote the gate to active FET source 441 and the active FET gate 443 to active FET drain capacitances, the capacitance of the inversion layer in a channel of the active FET sensor 440, and the charge at the interface between the active FET gate 443 oxide and the electrolyte (e.g., cerebrospinal fluid), respectively.

The active FET sensor 440 detects a biochemical reaction by translating the change in the net areal charge density (the change in the potential of the sensing gate $V_{sg}$) that the reaction causes into an electrical signal, for example, a threshold voltage $V_{th}$. Note that the shift in threshold voltage is generally measured relative to $V_{sg}$. In contrast, the active FET sensor 440 may include an electrolyte-gated ultrathin body silicon FET sensor with a double-gate configuration to enhance the sensitivity of the active FET sensor 440 beyond the so-called Nernst limit, as described in detail below, and allows for label-free measurement of biochemical (e.g., neurotransmitters such as dopamine) concentration.

When an analyte or biochemical (e.g., a dopamine) is in direct contact with the active FET gate 443, an electrical double layer capacitance is formed between the analyte and the active FET gate 443. The electrical double layer capacitance is connected in series with the quantum capacitance of the channel. The change in the total net charge as a result of the biochemical reaction will change the output characteristics of the active FET sensor 440. The modulation of the net charge may be achieved as a result of a reaction between the immobile ligands that are self-assembled on the surface of the active FET gate 443 and the mobile target analyte molecules in the solution. The active FET sensor 440 measures the change in the electron concentration as a result of the analyte (e.g., dopamine) redox process in the vicinity of the suspended sensing layer surface 442 (e.g., a suspended graphene sensing layer).

However, unlike the conventional cyclic voltammetry that measures the current flow due to the resultant electrons (amperometry), the active FET sensor 440 detects the change in the potential at the sensing layer 442 which serves as a sensing gate due to the change in the concentration of the redox electrons (potentiometry). This allows measurements without using an external reference electrode, which is bulky and inconvenient to use. The reference can be eliminated because the voltage bias applied to the suspended sensing layer 442 (e.g., graphene sensing layer) can be referenced with respect to the potential of the active FET source 441 region of the active FET sensor 440.

For example, the target analyte may include dopamine, and the voltage-dependent redox properties of dopamine molecules in the vicinity of the suspended sensing layer 442 may enable label-free detection of dopamine. It is to be appreciated that, at the end of each potential cycle, the original condition of the active FET sensor is restored. This characteristic, together with the label-free detection of dopamine, significantly simplifies consecutive measurements of dopamine.

Figure 10A:
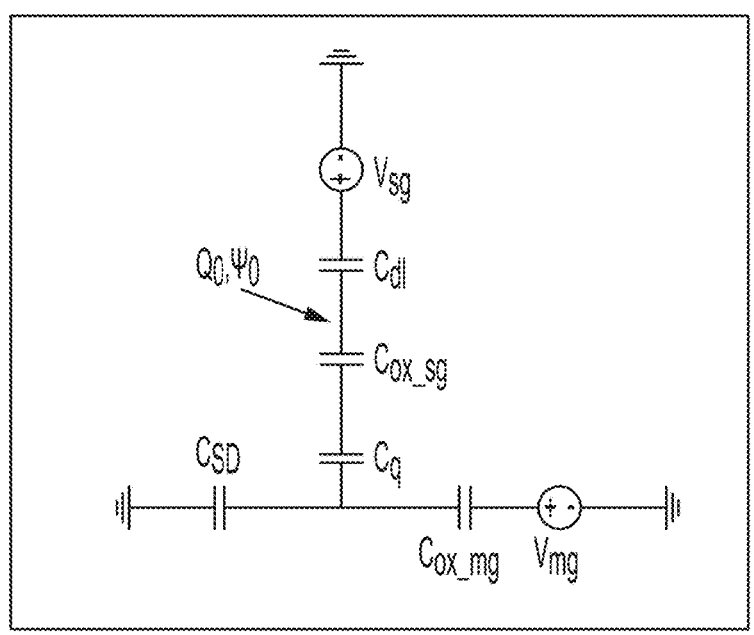
FIG. 10A is an equivalent capacitance model of the double-gated graphene FET sensor according to an embodiment.

A procedure for assessing the sensitivity of the active FET sensor 440 is to measure the shift in the threshold voltage of the device as a function of change in the pH of the solution ($\Delta V_{th}/\Delta pH$). The value of this parameter is a direct indication of the sensitivity of the FET sensor to the external charges (either positive or negative) that accumulate on its sensing surface as a result of the biochemical reaction. For a single-gate FET sensor, i.e. a conventional bulk silicon transistor, the change in the total charge in the bulk electrolyte, or, alternatively, the change in the proton concentration ($\Delta pH$), causes a threshold voltage shift given by:

$$\Delta V_{th} = -2.3 \frac{kT}{q} \propto \cdot \Delta pH \qquad (1)$$

where k is the Boltzmann constant, T is the temperature, q is the elementary charge, and a is a dimensionless sensitivity parameter. The sensitivity parameter ranges from 0 to 1 and is given by:

$$\propto = \left(\frac{C_{dl,ox}}{C_s} + 1\right)^{-1} \qquad (2)$$

where $C_{dl,o}$ denotes the liquid-gate capacitance and $C_s$ denotes the surface buffer capacitance. The liquid-gate capacitance is given by the series connection of the double-layer capacitance at the electrolyte-dielectric interface $C_{dl}$ with the gate oxide capacitance $C_{ox}$. The surface buffer capacitance, on the other hand, is determined by the density of active OH groups on the surface. From these equations, it can be observed that the sensitivity of conventional FET sensors is always smaller than 2.3 kT/q=59.9 mV/pH. For the active FET sensor 440, however, the pH-dependent shift in the threshold voltage can be measured relative to the active FET gate 443. FIG. 10A is the equivalent capacitance model for the double-gate active FET sensor 440 that operates in the linear regime, i.e. when the applied voltage between the active FET source 441 and the active FET drain 445 is small.

According to this model, the active FET sensor 440 acts as a voltage divider. Therefore, the change in the sensing layer 442 voltage can be described in relation to the change in the active FET gate 443 voltage. In this model, the inversion capacitance ($C_{inv}$) includes the contributions of both the electrostatic capacitance ($C_{es\_si}$) and the quantum capacitance ($C_q$) of the inversion layer. While $C_{es\_si}$ is related to the average distance of the channel electrons from the interface with the gate dielectric, $C_q$ is related to the density of states (DOS) of the two-dimensional electron gas (2-DEG) in the inversion layer. Note that $C_{inv}$ is much larger than other capacitances in the equivalent capacitance model shown in FIG. 10. Further, the value of CSD is negligibly small. Therefore, the relationship between the shift in the sensing layer 442 or sensing gate and the active FET gate 443 or measuring gate voltages as a result of the change in the net areal charge density on the sensing gate, i.e. $\Delta V_{mg}/\Delta V_{sg}$, is approximated by:

$$\frac{\Delta V_{mg}}{\Delta V_{sg}} \approx \frac{C_{dl,ox\_sg}}{C_{ox\_mg}} \quad (3)$$

where $C_{dl,ox\_sg}$ denotes the liquid-gate capacitance at the sensing layer 442 and $C_{ox\_mg}$ denotes the gate oxide capacitance of the active FET gate 443. The liquid-gate capacitance in the case of a double-gate active FET sensor 440 is given by the series connection of the $C_{dl}$ with the gate oxide capacitance of the sensing gate $C_{ox\_sg}$. For typical high-ion concentrations in a buffer solution, $C_{dl,ox}$ is almost equal to $C_{ox\_sg}$ since $C_{dl}$ is much larger than $C_{ox\_sg}$. Therefore $\delta V_{mg}/\delta V_{sg}$ is tantamount to the ratio of $C_{ox\_sg}$ to $C_{ox\_mg}$. This equation describes a key advantage of the double-gate active FET sensor 440. The active FET sensor 440 architecture in which $C_{ox\_sg}/C_{ox\_mg}$ is greater than 1 can enhance the sensor response to external charges beyond the Nernst limit. To implement this amplification of the biochemical signal, the equivalent oxide thickness (EOT) of the active FET gate is larger than that of the sensing gate, i.e., $EOT_{mg} > EOT_{sg}$.

Figure 10B:
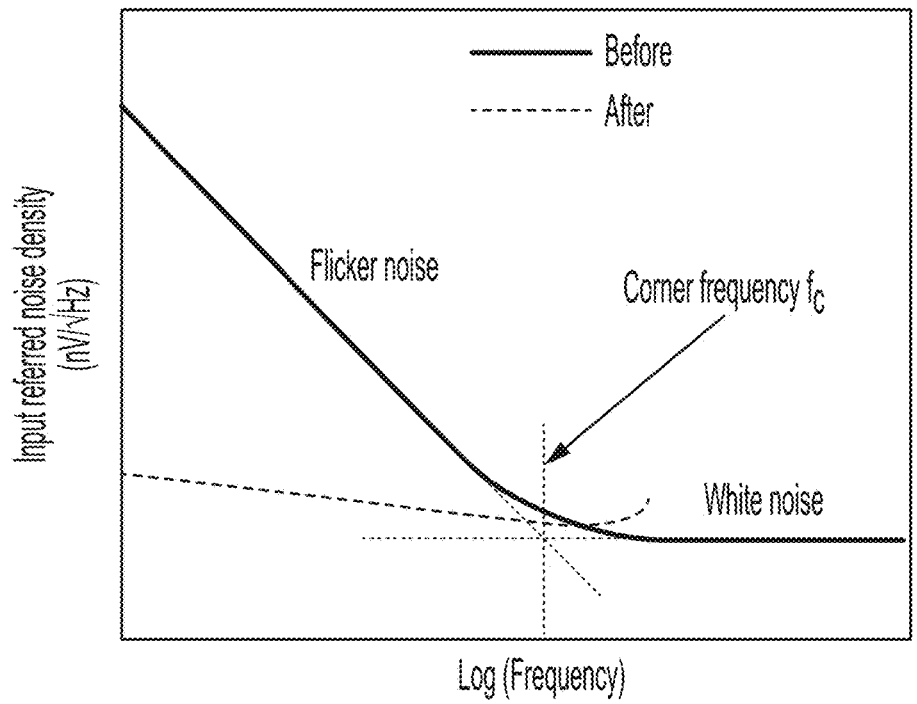
FIG. 10B is a plot of noise reduction of an op-amp transistor before and after noise reduction using a chopper stabilization technique.

As referenced above, one parameter that may determine the performance of a sensor is its noise characteristics. In some embodiments, the active FET sensor 440 is configured as the input transistor of a differential operational amplifier (op-amp), directly amplifying the input signal while improving the noise characteristics of the circuit: for example, using a chopper stabilizer as shown in FIG. 10B. As a result of the biochemical reaction, the flicker (1/f) noise, and the input referred dc offset voltage, the input signals are narrow-band, low-frequency signals, while thermal noise occupies a wide frequency band, as shown in FIG. 10B.

The origin of the flicker noise is attributed to the fluctuation of mobile charge carriers in the silicon channel due to trapping at the interface with the gate dielectric. Therefore, the quality of the interface between the gate oxide and the silicon channel plays an important role on the noise characteristics of the active FET sensor 440 and may be optimized during the device fabrication. In the case of the double-gate active FET sensor 440, the low-frequency noise behavior of the device will be influenced by the interfaces between the sensing oxide and the channel as well as the measuring oxide and the channel.

Figure 11A:
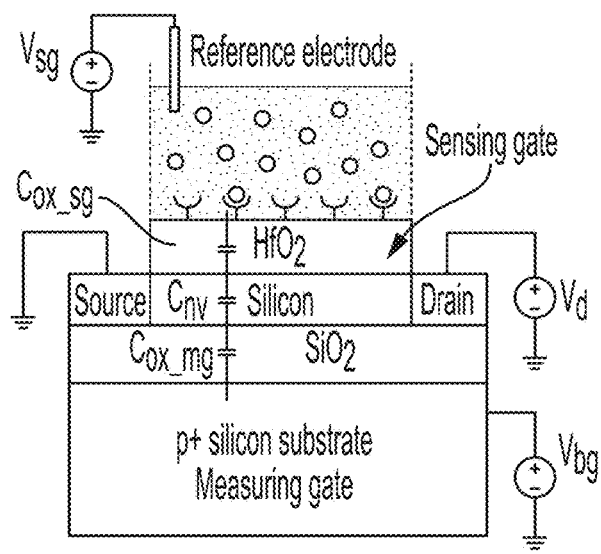
FIG. 11A is a schematic illustration of a fluidic device for probing electrical and electrochemical performance of the double gated graphene FET of FIG. 9.
Figure 11B:
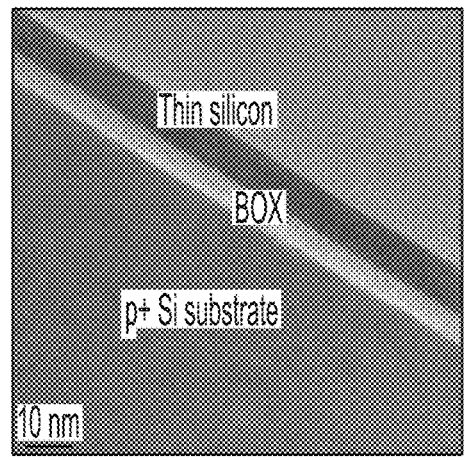
FIG. 11B is a cross-sectional transmission electron microscopy (TEM) image of a substrate including a 5 nm buried oxide (BOX) and a 7 nm layer of silicon disposed thereon.

FIG. 11A is a schematic illustration of a device for probing electrical and electrochemical performance of the double-gated active FET sensor 440 of FIG. 9. The active FET sensor 440 may be fabricated on a thin SOI substrate, for example, having an insulator which includes a 5 nm thick $SiO_2$ BOX layer, a 7 nm thick SOI layer, and a 760 µm thick substrate including p+silicon. FIG. 11B is a representative TEM image of the custom-made substrate, clearly illustrating various layers. Due to the strong effect of interface traps on the noise characteristics of the sensors, the interface trap density ($D_{it}$) between the BOX and the thin silicon layer may be measured from the transfer characteristics of the active FET sensor 440.

Figure 12A:
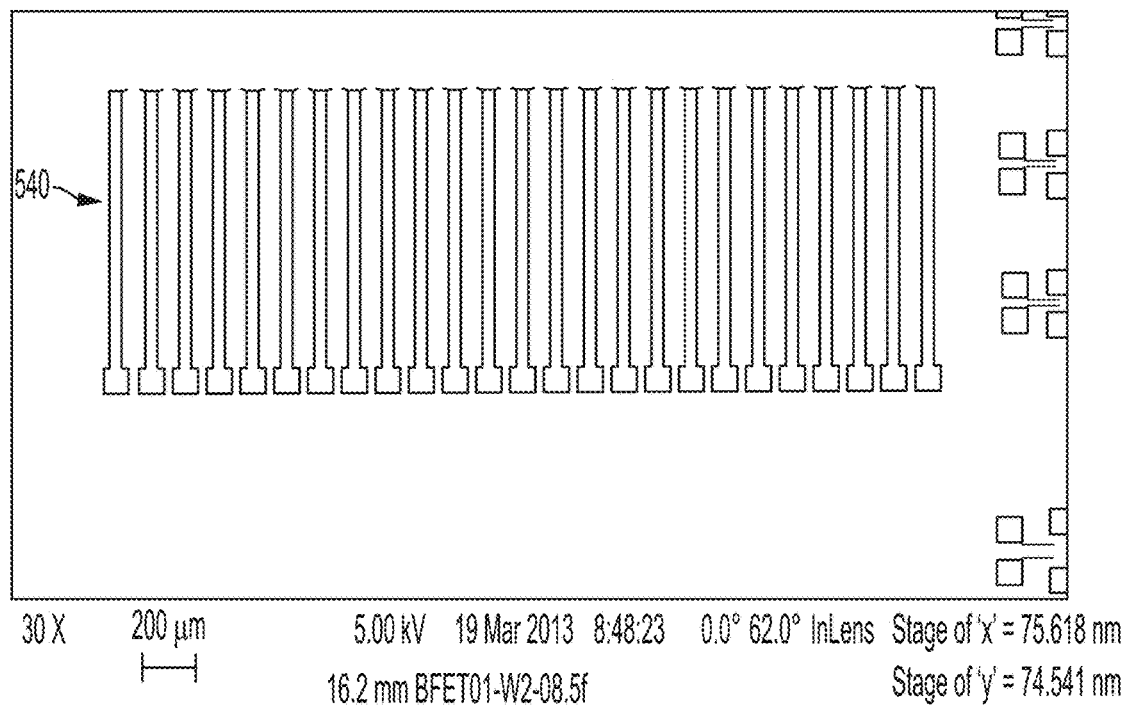
FIG. 12A is a top view SEM image of an array of double gated FET sensors.
Figure 12B:
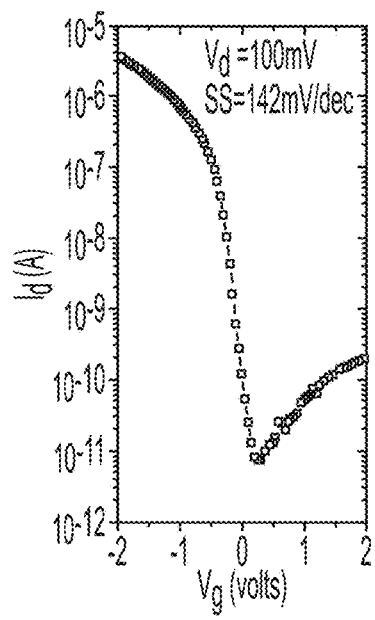
FIG. 12B is a current vs voltage plot of representative transfer characteristics of a p-type FET transistor used to determine an interface trap density between BOX and a silicon layer positioned thereon.
Figure 12C:
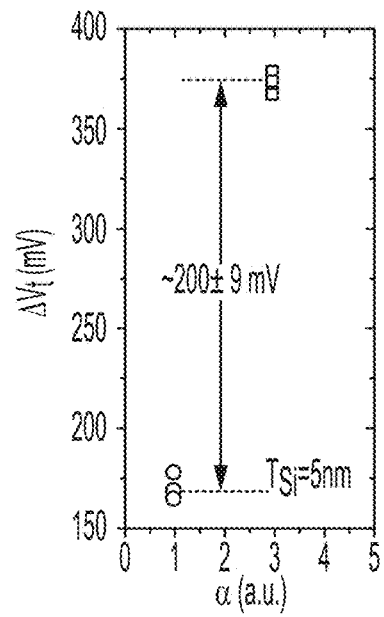
FIG. 12C is a plot showing more than two folds increase in sensitivity of a double gated graphene FET device by adjusting device parameters.

FIG. 12A is a top-view scanning electron microscope (SEM) image of an array of double-gated active FET sensors, as described herein. FIG. 12B is a plot of representative transfer characteristics of a p-type FET sensor used to determine the interface trap density between BOX and the thin silicon. FIG. 12C is a plot which indicates more than a two-fold increase in the sensitivity of the device achieved by adjusting the device parameters according to equation 4. The $D_{it}$ was extracted from the subthreshold characteristics of the device to be about $1,012 \text{ cm}^2\text{eV}^{-1}$ using the following equation:

$$S = 2.3\frac{kT}{q}\left(1 + \frac{C_D + C_{it}}{C_{ox}}\right) \quad (4)$$

where interface trap capacitance $C_{it}$ is equal to $qD_{it}$, assuming traps are uniformly distributed in the bandgap of silicon.

Experiments were performed for detecting glucose molecules using the active FET sensor device. The reaction between glucose molecules from an aqueous solution with boronic acid molecules assembled on the $HfO_2$ sensing gate results in negative charges. The results demonstrate the ability to adjust the sensitivity of the active FET device to the external charges by engineering the device parameters according to equation 4. In FIG. 12C, the sensitivity factor is defined as the ratio of the sensing capacitance $C_{ox\_sg}$ to the measuring capacitance $C_{ox\_mg}$. The shift in the threshold voltage of the sensor $\Delta V_t$ was used for assessing the performance (i.e., sensitivity) of the sensor. The plot indicates a significant enhancement of the device sensitivity by a factor of 2.15, which is consistent with the capacitance model presented in FIG. 10A. Each data point in FIG. 12C represents the measurement obtained from a device from a different sensor chip, indicating the reproducibility of the results.

Sensor Fabrication

In some embodiments, a plurality of sensor chips (e.g., the sensor chips 210) are fabricated together on a substrate and separated using a sacrificial layer etching and mechanical exfoliation process. For example, FIG. 13 is a schematic illustration of a method for fabricating a plurality of sensor chips on a substrate and separating individual sensor chips from the substrate. An integrated circuit consists of transistors and metal interconnects, where the transistors are wired together to perform a particular function. Although the total thickness of an integrated circuit is on the order of a few microns, the integration process is carried out on thick silicon substrates that are a few hundreds of microns.

The use of thick substrates facilitates handling and processing of silicon substrates in a manufacturing environment. The large thickness of the silicon substrates, however, renders them mechanically rigid. Reducing the thickness of these "hard" solid substrates is beneficial because it affords a higher degree of mechanical flexibility. Furthermore, thin semiconductors afford desirable properties for layer transfer and the assembly of a sensor assembly (e.g., the sensor assembly 100/200), which may include a sensor probe 102. For example, the steady-state energy release rate G for an interface crack in a bilayer system is given by:

$$G = \frac{(1-v^2)t\sigma^2}{E} \quad (5)$$

where v, E, t, and σ denote the Poisson's ratio, the Young's modulus, the thickness, and the stress of the thin film, respectively. The origin of the stress may be thermal and/or intrinsic. Equation 5 assumes that the thin film is placed on an infinitely thick substrate. The film delamination at the interface occurs when G>2Υ where Υ is the binding energy between the thin film and the substrate. Equation 5 indicates that the steady-state energy release rate decreases linearly as the thickness is reduced. Therefore this phenomenon can be utilized to heterogeneously integrate silicon membranes as thin as a few microns on foreign substrates even by van der Waals binding forces.

The key challenges for making mechanically flexible devices may include (i) devising an appropriate layer transfer strategy to produce thin semiconductor membranes, and (ii) developing handling methods for assembling thin semiconductor membranes after the release process. FIG. 13 is a schematic illustration of steps included in an example transfer process, which may be used to separate a plurality of sensor chips fabricated on a substrate. In Step 1, a handle substrate including a stack of silicon/germanium/silicon is provided, which is fabricated using any suitable process. For example, the germanium may be grown on silicon substrate using an ultra-high-vacuum chemical vapor deposition (UHVCVD) process, followed by growth of another silicon layer on top of the germanium so as to obtain the silicon/germanium/silicon stack. At least a portion of the top silicon layer is oxidized so as to obtain a SOI layer (i.e., a silicon layer disposed on an insulating silicon oxide layer).

Once the substrate fabrication process is complete, in Step 2, active FET sensors or any other sensor may be fabricated in the SOI layer: for example, using standard complementary metal-oxide-semiconductor (CMOS) integration processes. This is followed by a metallization step in order to make Ohmic contacts to the CMOS sensors. Integrated microelectrode sensors/actuators for electrophysiological recording and stimulation, together (e.g., PtSi$_2$ sensors) with the active FET sensors, are fabricated on each sensor chip, so as to form a plurality of sensor chips on the substrate. It is to be appreciated that while FIG. 13 shows only two sensor chips (chip 1 and chip 2) disposed on the substrate, any number of sensor chips may be fabricated on the substrate.

In Step 3, the borders of the sensor chips are defined (e.g., using photolithography) followed by the formation of trenches in the SOI layer and the buried silicon oxide layer around the periphery of the chips in order to access the embedded germanium layer. The germanium layer serves as a sacrificial layer and in Step 4, the germanium sacrificial layer is partially etched, for example in a dilute hydrogen peroxide solution, which is innocuous to other constituent elements of the integrated circuit). However, the germanium sacrificial layer is not fully removed. Instead, the germanium layer is only partially etched so that the thin sensor chips, consisting of the active and passive sensors, are anchored on narrow germanium pillars.

Mechanical exfoliation is then performed by applying a soft polymer (e.g., polydimethylsiloxane (PDMS)) stamp onto the sensor chips. The soft polymer removably adheres to the sensor chips, for example, via Van der Waals interaction or stiction, with sufficient adhesive force such that stripping of the polymeric stamp from the substrate detaches the weakly anchored sensor chips from the germanium pillars.

Referring again to FIG. 3C, the second insulating layer 203, which forms the top surface of the silicon substrate 202 of the sensor assembly 200 includes silicon dioxide which promotes adhesion with the sensor chips (e.g., the sensor chip 210) including the electrophysiological first sensor 220, and the electrochemical second sensor 240, through the hydroxylation of the surface. The sensor chips mechanically exfoliated using the polymeric stamp as illustrated in FIG. 13, may be transferred from the polymeric stamp onto a second polymeric substrate (e.g., second PDMS substrate) before the final transfer onto the second insulating layer 203 of the substrate 202.

Due to the poor adhesion of the sensor chips to the second polymeric substrate, the polymeric substrate easily detaches from the chips via gentle mechanical force. In some embodiments, the dimensions of each sensor chip are about 300 μm by 100 μm. In some embodiments, custom-made jigs and/or fixtures are used to align the second polymeric stamp and, thereby the sensor chips on the second insulating layer 203 of the substrate 202. The jigs/fixtures provide alignment accuracy in the range of few tens of microns. Once the sensor chips are positioned on the substrate 202, the first electrode 221 and the second electrodes 241 are deposited on the second insulating layer 203 so as to electrically couple the first sensors 220 and the second sensors 240 fabricated on each of the sensor chips 210 to electronic circuitry (e.g., the control circuitry 170, the global controller 192 or external electronics) for recording the signals. The first electrodes 221 and the second electrodes 241 are then subsequently covered using biocompatible polymers (e.g., parylene) or any other insulating layer (e.g., SiO$_2$) so as to prevent electrical shorts.

Figure 22:
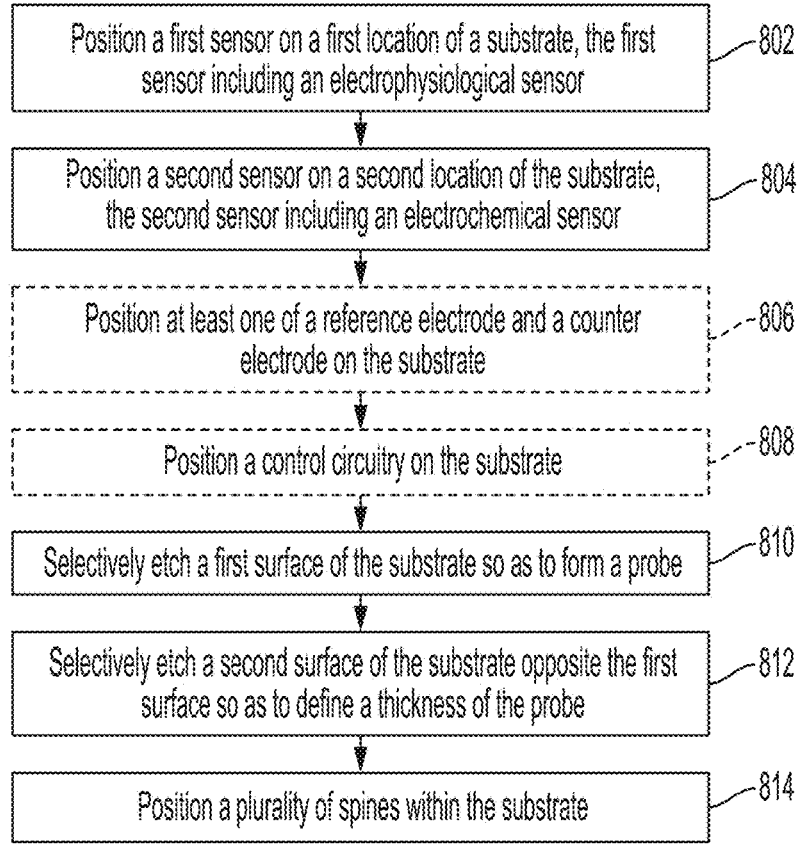
FIG. 22 is a schematic flow diagram of an example method for fabricating a sensor assembly.

FIG. 22 is a schematic flow diagram of an example method 800 of fabricating a sensor assembly (e.g., the sensor assembly 100/200/700 or any other sensor assembly described herein). The method includes positioning a first sensor which includes an electrophysiological sensor, on a first location of a substrate at 802. For example, the first sensor 120/220/320/720 may be positioned or fabricated on the substrate 102/202/302/402/702. In some embodiments, the first sensor includes a plurality of silicon nanopillars or PtSi$_2$ nanopillars as described herein. The substrate may include a SOI layer and positioning the first sensor on the substrate may include fabricating the plurality of PtSi$_2$ nanopillars on the substrate, as described before herein.

A second sensor, which includes an electrochemical sensor, is positioned on a second location of the substrate at 804. For example, the second sensor 140/240/340/440/540/640/740 is positioned on the second location of the substrate 102/202/302/402 702. In some embodiments, the substrate includes a SOI layer having an insulating layer positioned thereon. The second sensor comprises a sensing layer (e.g., the sensing layer 342/442) such as a graphene disc or graphene nanoribbon, which is disposed on the insulating layer. In some embodiments, a cavity (e.g., the cavity 346/446) is defined in the insulating layer below the sensing layer so as to define an air gap between the sensing layer and the SOI layer. Furthermore, an active field effect transistor (FET) (e.g., the active FET sensor 440) may be fabricated in the SOI layer. The active FET includes an active FET source, an active FET gate and an active FET drain. The active FET gate is positioned below the cavity such that the air gap exists between the active FET gate and the sensing layer, and the sensing layer provides a second gate of the active FET, as described herein.

With continued reference to FIG. 22, a reference electrode and/or a counter electrode are positioned on the substrate at 806. Furthermore, a front-end circuitry (e.g., the front-end circuitry 170/670) may also be positioned on the substrate at 808. In particular embodiments, the first sensor 120/220/320, the second sensor 140/240/340/440/540/640/740, the reference electrode (e.g., the reference electrode 630), the counter electrode (e.g., the counter electrode 650) and/or the front-end circuitry (e.g., the front-end circuitry 170/670) is fabricated on an integrated sensor chip which is then disposed on the substrate 102/202/302/402/702.

A first surface of the substrate is selectively etched so as to form a probe 810. A second surface of the substrate opposite the first surface is also selectively etched so as to define the thickness of the probe 812. A plurality of spines are disposed within the substrate at 814. For example, the first surface and the second surface of the substrate 102/202/302/402/702 or any other substrate described herein may be selectively etched to define the thickness of the probe as described in FIG. 4A. Metallic spines 160/260 (e.g., gold spines) may then be disposed within the substrate 102/202/302/402/702 so as to provide mechanical strength and rigidity to the substrate 102/202/302/402/702 as described herein. In some embodiments, the first surface and the second surface of the substrate may be etched and/or the metallic spines may be defined in the substrate prior to disposing the first sensor, the second sensor, the reference electrode, the counter electrode, the control circuitry, and/or a sensor chip thereon.

Figure 23:
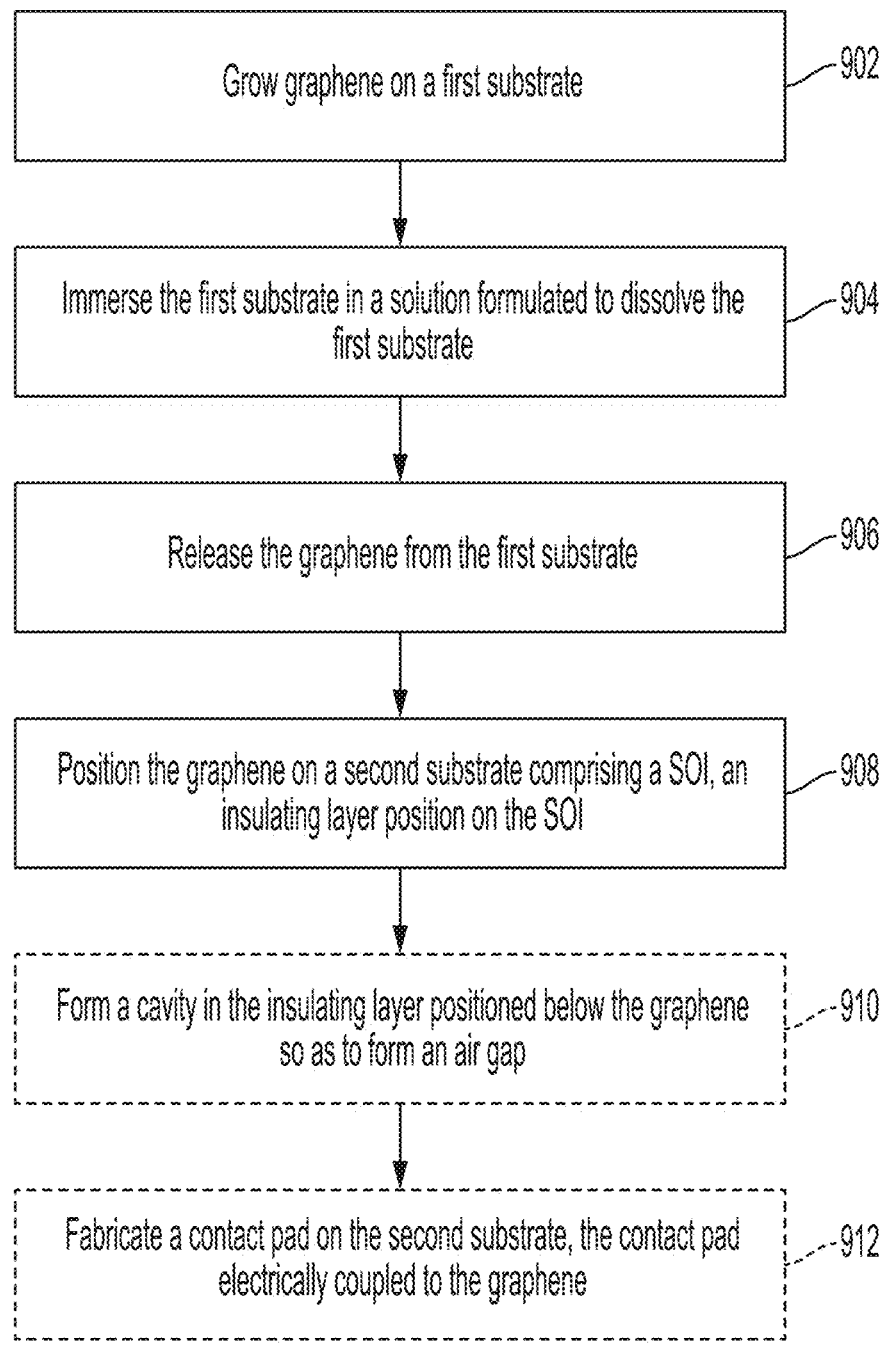
FIG. 23 is a schematic flow diagram of an example method for fabricating a graphene electrochemical sensor.

FIG. 23 is a schematic flow diagram of an example method 900 for forming a graphene electrochemical sensor, for example the second sensor 140/240/340/440/540/640/740 or any other graphene electrochemical sensor described herein. The method comprises growing graphene on a first substrate at 902. In the method of FIG. 23, graphene is epitaxially grown on the first substrate. In some embodiments, the first substrate includes nickel. The first substrate is immersed in a solution formulated to dissolve the first substrate at 904. For example, the first substrate includes nickel and the solution includes ferric chloride, which selectively dissolves nickel.

The graphene is released from the first substrate at 906. The releasing may include mechanically exfoliating the graphene from the first substrate after a bulk of the first substrate is dissolved. The graphene is positioned on a second substrate at 908. The second substrate includes an SOI layer and an insulating layer positioned on the SOI layer and may include, for example, the substrate 102/202/302/402/702 or any other substrate described herein. The graphene is positioned on the insulating layer. In some embodiments, the solution, for example, the ferric chloride solution, is sufficient to completely dissolve the first substrate, for example, nickel so that the epitaxially grown graphene is released from the first substrate during operation 904.

In some embodiments, the method 900 includes forming a cavity in the insulating layer at 910. The cavity (e.g., the cavity 346/446) is positioned below the graphene so as to define an air gap between the graphene and the SOI layer. In some embodiments, the cavity 346/446 is defined prior to positioning of the graphene on the second substrate such that the graphene is positioned on and overlays the cavity 346/446.

In particular embodiments, an active field effect transistor (FET) is fabricated in the SOI layer at 912. The active PET (e.g., the active FET sensor 440) includes an active PET source, an active FET gate and an active FET drain. The active FET gate may be positioned below the cavity 346/446 such that the cavity defines an air gap interposed between the active FET gate and the graphene. The graphene provides a second gate of the active PET. In sonic embodiments, contact pads are formed on the second substrate. The contact pads are electrically coupled to the graphene (e.g., via the first electrode 221).

Figure 24:
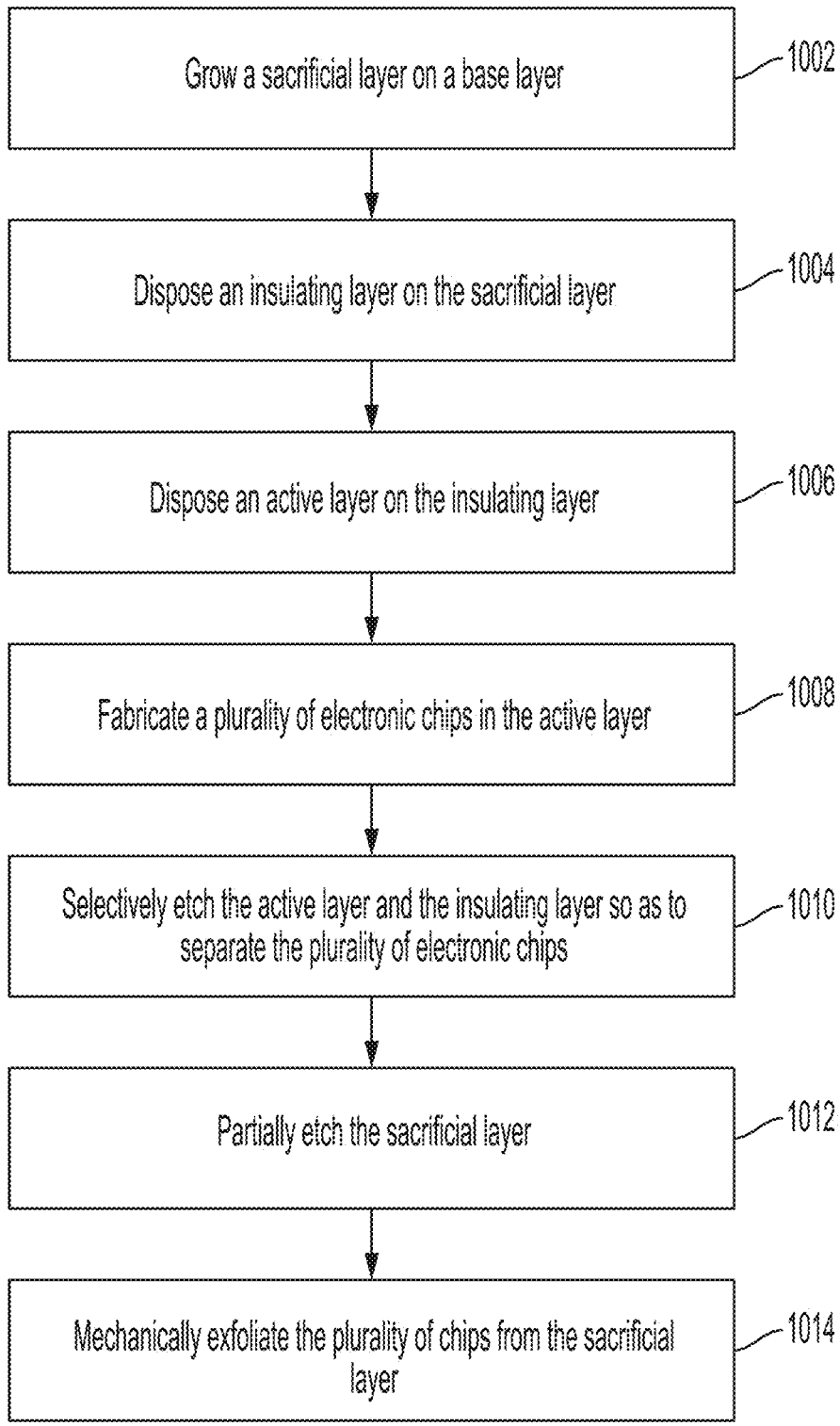
FIG. 24 is a schematic flow diagram of an example method for fabricating a plurality of electronic chips on a substrate and separating the plurality of electronic chips therefrom.

FIG. 24 shows a schematic flow diagram of an example method 1000 of fabricating a plurality of sensor chips (e.g., the sensor chips 210/710) on a substrate, and removing the sensor chips therefrom. The method 1000 comprises growing a sacrificial layer on a base layer at 1002. As a nonlimiting example, the base layer includes silicon and the sacrificial layer includes germanium, such as deposited on the silicon layer via a UHVCVD process. An insulating layer is disposed on the sacrificial layer at 1004. For example, a silicon oxide layer may be disposed on the germanium layer.

An active layer is disposed on the insulating layer at 1006. The active layer may include an SOI layer. In some embodiments, an active layer may be disposed on the sacrificial layer and a portion of the active layer in contact with the sacrificial layer may be transformed into the insulating layer. For example, a silicon active layer may be disposed on a germanium sacrificial layer, and a portion of the silicon active layer in contact with germanium is subsequently oxidized to produce a SOI active layer.

A plurality of electronic chips are fabricated in the active layer at 1008. The electronic chips may include, for example, the sensor chips 110/210/710 that are fabricated in or on the active layer, or any other electronic chip, for example a VLSI circuit. The plurality of sensor chips may include an electrophysiological sensor (e.g., the first sensor 120/220/320) and/or an electrochemical sensor (e.g., the second sensor 140/240/340/440/540/640/740). The electronic chips may also include a counter electrode (e.g., the counter electrode 650), a reference electrode (e.g., the reference electrode 630) and/or a control circuitry (e.g., the front-end circuitry 170/670/770).

The active layer and the insulating layer are etched so as to separate the plurality of electronic chips at 1010. For example, a perimeter of each electronic chip may be etched using RIE, DRIE and/or wet etching so as to separate the plurality of electronic chips. The sacrificial layer is partially etched at 1012. For example, the sacrificial layer may include germanium which may be partially etched using dilute hydrogen peroxide so as to leave each of the plurality of electronic chips attached to a thin pillar of germanium, as shown and described with respect to FIG. 13.

The plurality of electronic chips are mechanically exfoliated from the sacrificial layer at 1014. For example, a polymeric membrane (e.g., a PDMS membrane) may be positioned on the plurality of electronics chips so as to contact the active layer such that the active layer removably adheres to the polymeric membrane. The polymeric membrane is stripped from the partially etched sacrificial layer so as to detach the plurality of electronic chips from the partially etched sacrificial layer. The polymeric membrane may be positioned on a substrate such that the insulating layer included in the plurality of electronic chips contacts the substrate and sticks to the substrate (e.g., the substrate 102/202/302/402/702). For example, a van der Waals force or stiction between a silicon oxide layer positioned on back surface of an electronic chip and a silicon/silicon oxide substrate may be greater than the van der Waals force and/or stiction between the polymeric membrane and the active layer of the plurality of chips. The polymeric membrane may be stripped from the substrate so as to leave the plurality of electronic chips positioned on the substrate.

Front End Circuitry

Figure 2:
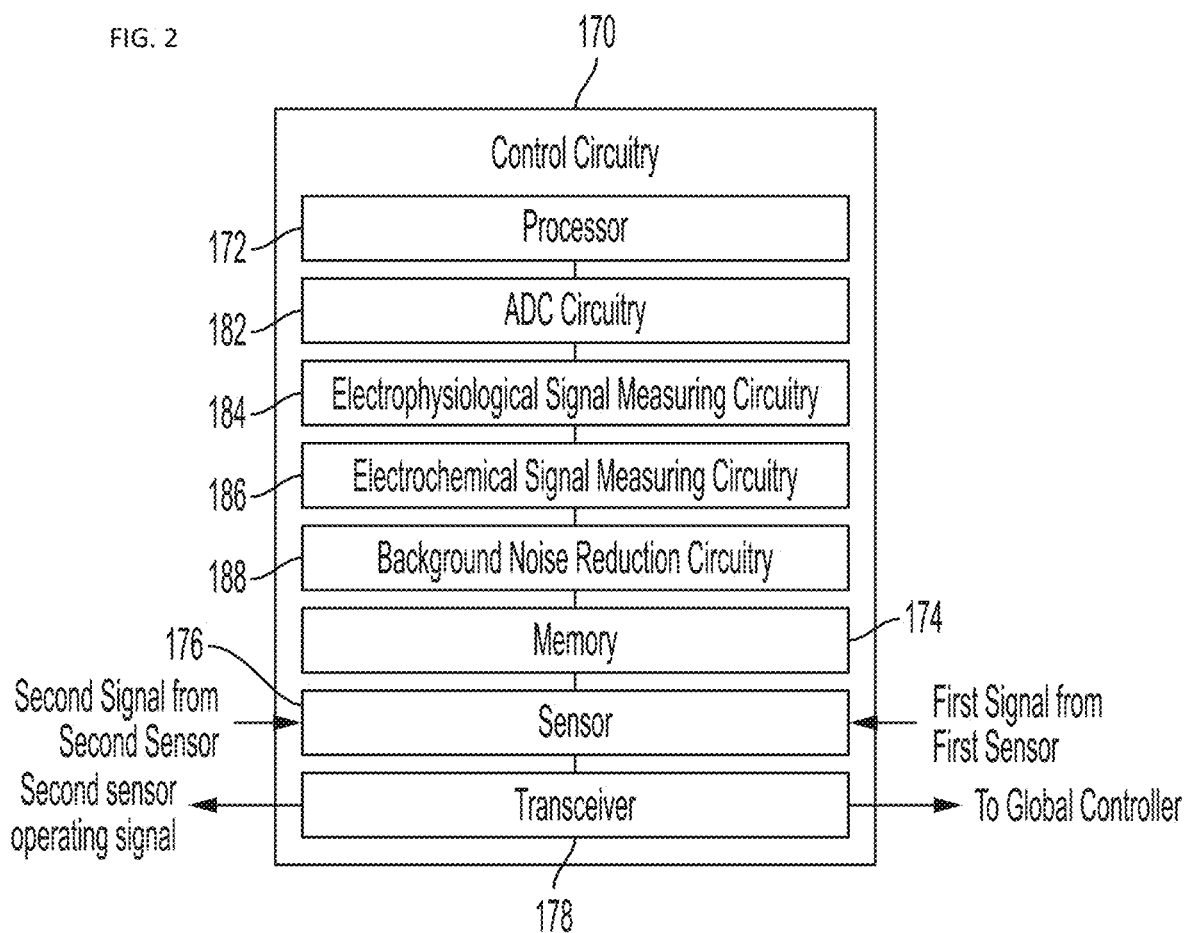
FIG. 2 is a schematic block diagram of one embodiment of a front-end circuitry in the sensor assembly of FIG. 1.

As previously noted, the system 100 includes front end circuitry 170 as illustrated in FIG. 1. FIG. 2 is a schematic block diagram showing various components which may be included in the front-end circuitry 170. As shown in FIG. 2, the front-end circuitry 170 includes a processor 172, a memory 174 or any other non-transitory computer readable medium, a sensor 176, a transceiver 178, an ADC circuitry 182, an electrophysiological signal measuring circuitry 184, a signal measuring circuitry 186, and a background noise reduction circuitry 188.

The processor 172 can include a microprocessor, a programmable logic controller (PLC) chip, an ASIC chip, or any other suitable processor. The processor 172 is in communication with the memory 174 and configured to execute instructions, algorithms, commands or otherwise programs stored in the memory 174.

The memory 174 includes any of the memory and/or storage components discussed herein. For example, memory 174 may include RAM and/or cache of processor 172. The memory 174 may also include one or more storage devices (e.g., hard drives, flash drives, non-transitory computer readable media, etc.) either local or remote to controller 170. The memory 174 is configured to store look-up tables, algorithms, or instructions.

As described before with respect to FIG. 2, the front-end circuitry 170 includes an ADC circuitry 182 configured to convert analog signals corresponding to the electrophysiological and electrochemical signals, to digital signals. The sensor 176 is configured to sense or detect a first signal from the first sensor 120 and a second signal from the second sensor 140. The first signal which includes an electrophysiological signal, and the second signal which includes an electrochemical signal, may include a current or a voltage. The sensor 176 communicates the first signal which includes the electrophysiological signal, and the second signal which includes the electrochemical signal, to the ADC circuitry 182. Each of the electrophysiological signal and the electrochemical signal may include an analog signal. The ADC circuitry 182 is configured to convert the first signal and the second from analog signals to digital signals. In some embodiments, the ADC circuitry 182 includes an integrator circuit configured to locally convert an analog current signal into an analog voltage signal (e.g., switched capacitor integrated circuit). A dynamic range of the integrator circuit may be adjusted by an integration time of the switched capacitor integrator circuit.

With continued reference to FIG. 2, the electrophysiological signal measuring circuitry 184 is configured to measure a first signal from the first sensor 120, i.e., an electrophysiological signal corresponding to action potentials or local field potentials detected in the portion of the brain. The background noise reduction circuitry 184 may include a band pass filter configured to filter noise from the first signal. In some embodiments, the electrophysiological signal measuring circuitry 184 also is configured to provide a stimulating electrical signal to the first sensor 120, for example, to stimulate neurons of a portion of a brain in which the sensor assembly 100 is inserted. The stimulating electrical signal evokes the electrophysiological signal which may then be measured by the first sensor 120. The electrochemical signal measuring circuitry 186 is configured to provide an operating signal to the second sensor 140 such as the voltammetry scan signal to the second sensor 140. For example, the target chemical may include dopamine, and the voltammetry signal may be configured to cause an oxidation/reduction of the dopamine so as to generate an electrochemical signal (e.g., a current) corresponding to the concentration of the dopamine. In some embodiments, the voltammetry scan signal may include a voltage ramp rate in a range of 0.1 Volt per second to 2,400 Volts per second (e.g., include a fast scan cyclic voltammetry (FSCV) signal).

Furthermore, with continued reference to FIG. 2, the front-end circuitry 170 may also include a background noise reduction circuitry 188 configured to subtract the background current from the signals (e.g., the first signal corresponding to electrophysiological measurements, and the second signal corresponding to electrochemical measurements) and auto-zero at least a component of the second signal so as to cancel a voltage offset included in the second signal and reduce low frequency noise.

The voltammetry scan signal may comprise a dual-slope voltage ramp signal configured to cause the electrochemical reaction which produces the electrochemical signal in the second sensor 140. The electrochemical signal may include a background current and an electrochemical current corresponding to the concentration of the chemicals (e.g., the neurotransmitter dopamine). Furthermore, the background noise reduction circuitry 188 may be further configured to generate a subtraction signal (e.g., via one or more adjustable, low-noise and high-precision current source) that has an opposite polarity to the background current and an amplitude that partially subtracts the background current from the second signal (i.e., the electrochemical signal). The electrochemical signal-measuring circuitry 186 may determine a concentration of the chemical from the second signal. In some embodiments, the background noise reduction circuitry 188 includes an auto-zero mechanism. In such embodiments, the background noise reduction circuitry 188 is configured to subtract an offset voltage on the integrator circuit through the auto-zero mechanisms, and sample the electrochemical signal at a predetermined frequency so as to reduce the low-frequency flicker noise.

In this manner, the background noise reduction circuitry may filter noise from the first signal and the second signal so as to generate a filtered first signal and a filtered second signal, respectively. The filtered first signal and the filtered second signal may be communicated to the global controller 192, for example via the transceiver 178. For example, the transceiver 178 may include a communication circuitry configured to communicate the first filtered signal and the second filtered signal to the global controller 192 via hard wired leads, Bluetooth®, low powered Bluetooth®, Wi-Fi or any other suitable communication means.

In some embodiments, the front-end circuitry 170 includes a timing circuitry (further described below) configured to instruct the electrochemical signal measuring circuitry 186 to alternatively provide a voltammetry scan signal, as described herein, to the second sensor 140 (i.e., the electrochemical sensor) for a first time so as to measure the electrochemical signal corresponding to the concentration of dopamine or any other target analyte. The timing circuitry may be further configured to instruct the electrophysiological signal measuring circuitry 184 to measure the electrophysiological signal via the electrochemical sensor for a second time, thereby alternatively measuring the electrochemical signal and the electrophysiological signal via the second sensor 140. In such embodiments, the first sensor 120 is excluded.

Figure 14A:
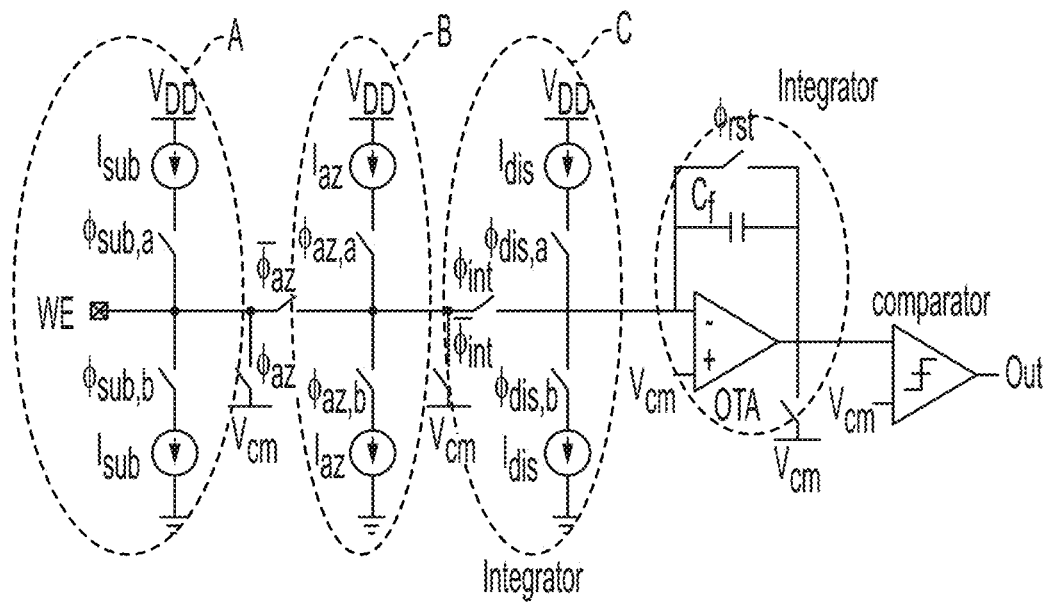
FIG. 14A is a schematic illustration of a dual slope analog to digital conversion (ADC) circuitry including a current subtraction and auto-zero circuit.

For example, FIG. 14A is a schematic illustration of a dual slope analog to digital conversion (ADC) circuitry including a current subtraction and auto-zero mechanism which may be used as the ADC circuitry 182 as well as the background noise reduction circuitry 188 of the front-end circuitry 170. The background current during amperometric measurements may be large, for example, larger than the electrochemical current corresponding to the concentration of the analyte (e.g., dopamine).

Generally, the ADCs used for electrochemical sensing have a large dynamic range and consume a lot of power. In contrast, the ADC circuitry of FIG. 14A is configured to dynamically subtract a fixed average from the background current such that the ADC circuitry has a much smaller dynamic range of 2 nAmp to 100 nAmp and smaller power consumption. The portion of the ADC circuitry of FIG. 14A indicated by the arrow A includes one or more low noise, high precision voltage sources $V_{DD}$. The voltage sources $V_{DD}$ may generate a subtraction signal having an opposite polarity to background current so as to subtract the background current from the total current signal. The amplitude of the subtraction signal may partially cancel the background current signal.

The portion of the ADC circuitry of FIG. 14A indicated by the arrow B includes the auto-zero mechanism configured to subtract and offset voltage on the integrator circuit. The integrator circuit comprises a switched capacitor integrator circuit. A dynamic range of the ADC circuitry may be adjusted by the integration time of the switched capacitor integrator circuit. Furthermore, a portion of the ADC circuitry indicated by the arrow C may include a plurality of switches configured to sample the electrochemical signal at a predetermined frequency so as to reduce flicker noise.

Figure 14B:
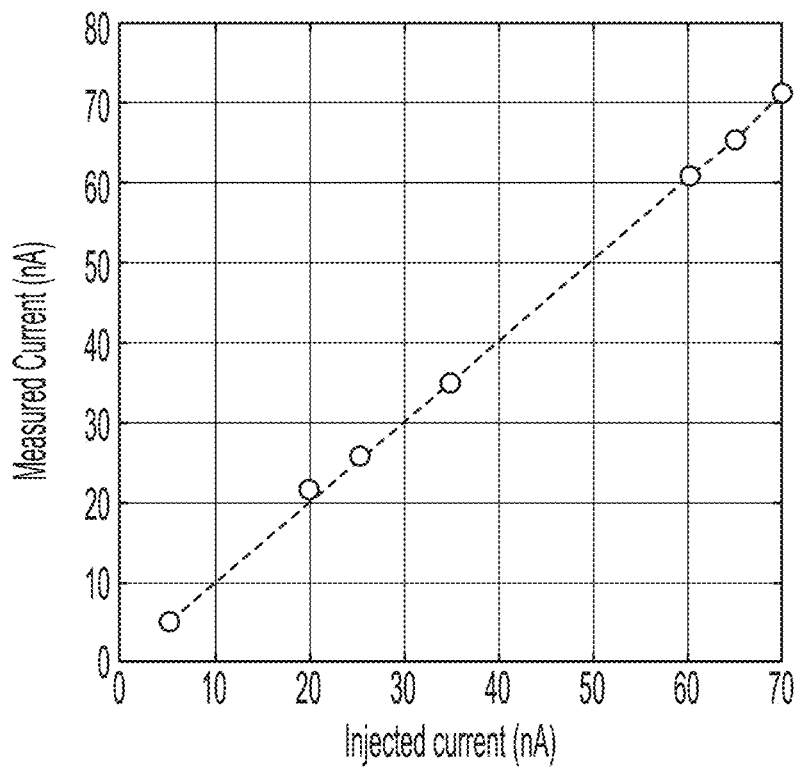
FIG. 14B is a plot of preliminary measurement results of an ADC circuitry fabricated using 65 nm technology.

FIG. 14B is a plot of preliminary measurement results of an ADC circuitry fabricated using 65 nm technology. Dopamine was used as the target analyte. As can be seen in FIG. 14B, the background non-faradic current is significantly larger than the current that is produced by the electrochemical reaction between dopamine molecules and carbon atoms. The dopamine concentration is linearly proportional to the amplitude of the electrochemical current.

Therefore, the improved detection limit of dopamine translates into the implementation of a high-resolution ADC. On the other hand, the large background current necessitates an ADC with large dynamic range. Generally, the large dynamic range is accounted for by significantly increasing the power consumption of the ADC which is not desirable for neurotransmitter sensing. The dual slope ADC circuitry illustrated in FIG. 14A dynamically subtracts the background current, achieving high resolution without increased power consumption for voltammetry scan measurements (e.g., voltammetry scans comprising a voltage ramp rate in a range of 0.1 Volts per second to 2,400 Volts per second). The resolution of the ADC is about or better than 200 picoamps.

FIG. 15 is a schematic block diagram of an integrated sensor platform including a front-end circuitry 670 which is coupled to a user interface via a global controller 692. The front-end circuitry 670 may be integrated on a sensor chip (e.g., the sensor chip 210 using VLSI technology). The sensor chip may also include a first working electrode 620 (e.g., an electrophysiological signal measuring electrode such as the first electrode 120/220) and/or a second working electrode 140 (e.g., an electrochemical signal measuring electrode such as the second electrode 140/240/340/440). A single reference electrode 630 may be used as the reference electrode for each of the first working electrode 620 and the second working electrode 640 and may also be fabricated on the sensor chip. Furthermore, a counter electrode 650 may also be fabricated on the sensor chip (e.g., a platinum, carbon or graphene counter electrode).

The front-end circuitry 670 includes an electrophysiological readout circuitry 680 electrically coupled to the first working electrode 620. The electrophysiological readout circuitry 680 includes a first ADC for locally converting analog electrophysiological signals to digital signals, a bandpass filter for noise reduction, and a low noise amplifier. The front-end circuitry 670 also includes a FSCV readout circuitry 682 electrically coupled to the second working electrode 640. The FSCV readout circuitry includes a second ADC, a 1/f noise or flicker noise filter, and an amplifier.

The front-end circuitry 670 may include a plurality of electrophysiological readout circuitries 680 and a plurality of FSCV readout circuitries, each of which is electrically coupled to a global digital controller 692, for example, a signal multiplexer or an amplifier. The global digital controller 692 is coupled to a user interface 694 (e.g., the computing device 2030), which may interpret and display the electrophysiological and electrochemical signals to a user. The global digital controller 692 also outputs a signal to a dual-slope ramp generator circuitry 684 that may also be defined on the sensor chip. The dual-slope ramp generator circuitry 684 includes a switched-capacitor integrator circuit including a timing controller, a FSCV memory, a digital to analog circuitry (DAC), and an operational amplifier. The dual-slope ramp generator circuitry 684 is configured to supply electrons back into the electrolyte (e.g., cerebrospinal fluid) via the counter electrode 650 so as to complete the circuit. Thus, the front-end circuitry 670 allows local conversion of the FSCV current signal measured by the miniaturized first working electrode 620 and the second working electrode 640 to a commensurate voltage signal close to the location where the signal is generated. This conversion may reduce the noise, particularly when a sensor assembly (e.g., the sensor assembly 100/200) includes long neural probes (e.g., for electrophysiological and chemical signal measurements in brains of humans and non-human primates).

Figure 16A:
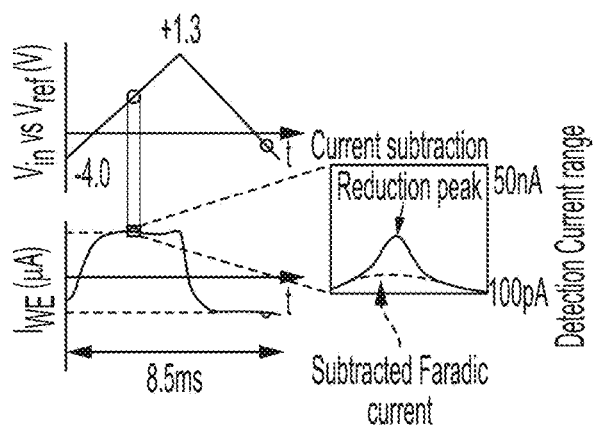
FIG. 16A are plots illustrating a current subtraction scheme for improving an ADC resolution.
Figure 16B:
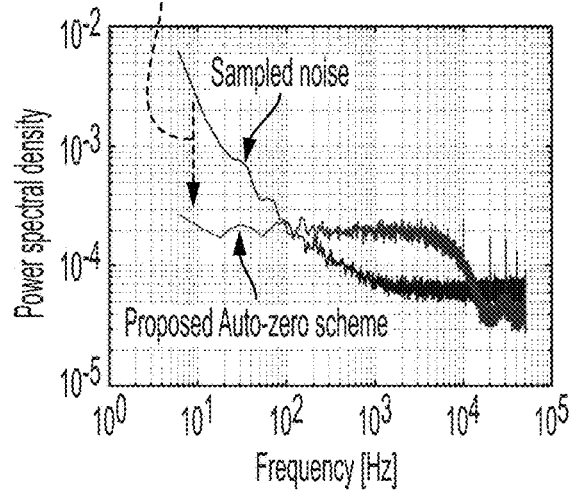
FIG. 16B is a plot of simulation results demonstrating the effectiveness of the auto zero circuitry for reducing flicker (1/f) noise.

The dual-slope ADC architecture described herein is suitable for high-resolution measurements at a moderately low sampling rate and allows low-power operation. However, it poses a trade-off between the resolution and the detection range of the input current signal. FIG. 16A illustrates a current subtraction scheme for improving an ADC resolution; FIG. 16B shows simulation results demonstrating the effectiveness of the auto zero circuitry for reducing flicker (1/f) noise. In FSCV measurements, a dual-slope voltage ramp is applied to the working electrode (FIG. 16A). The voltage ramp produces two current signals: non-faradic background current, and electrochemical current (See FIGS. 8C and 8D) due to oxidation/reduction of the target analyte (e.g., dopamine) on the surface of the working electrode. The electrochemical current depends on the concentration of the target analyte. The non-faradic background current, however, is independent of the target analyte concentration and is produced by charging and discharging of the electrical double layer at the electrode interface.

To improve the lower detection limit of FSCV, a novel current subtraction scheme is implemented to compensate for the non-faradic background current before sampling the current signal by the ADC, which is illustrated in FIG. 16A. Subtraction of the large background current removes the need for a very large maximum detection range because the subtracted current has a much smaller range than the total current. The resolution of the ADC may, therefore be improved by focusing on the relevant range for the subtracted current. For accurate operations of a switched-capacitor integrator circuit, an auto-zero (AZ) step is added to cancel out offset voltages caused by accumulation of stray charges. The AZ circuitry described herein allows improved sampling scheme by performing two functions simultaneously: (i) dynamic cancellation of the voltage offset and (ii) reduction of low-frequency (flicker or 1/f) noise. The plot in FIG. 16B shows numerical simulations of the noise power spectral density for the AZ circuitry, demonstrating significant reduction of the flicker noise without compromising the white noise (the flat part of the noise spectrum). These results indicate that the AZ circuitry described herein may be used effectively as a noise canceling technique such as correlated double sampling. Furthermore, chopper stabilizer circuits may also be incorporated to further reduce the low-frequency noise.

Figure 17:
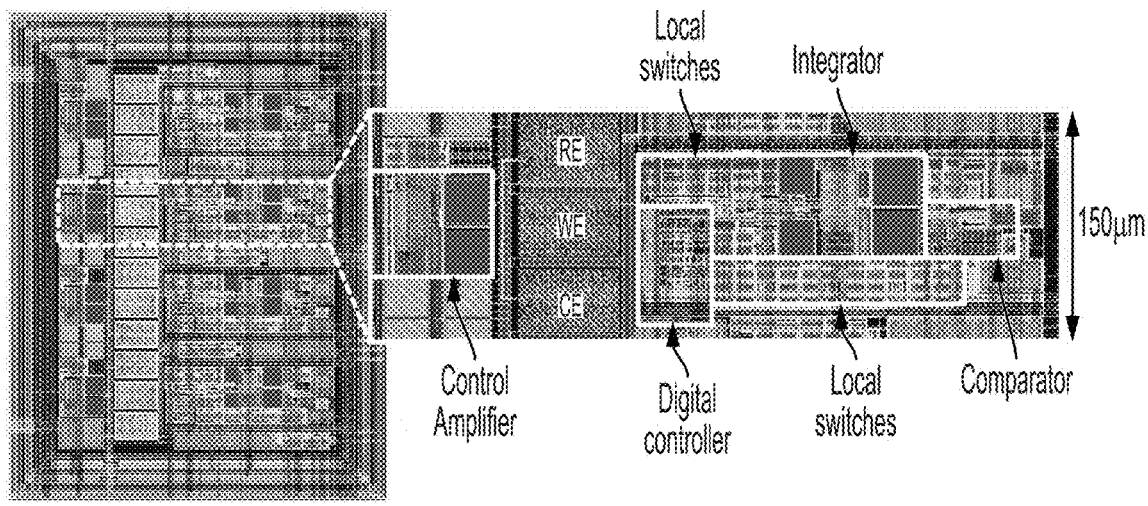
FIG. 17 is a circuit lay out of a controller circuitry including four independent FSCV measurement channels.

FIG. 17 illustrates a top view layout of a prototype front-end circuitry for fabrication using a 65 nm silicon manufacturing technology. The prototype chip consists of four independent channels which allow investigation of the effects of electrode area on the voltammetry measurements. In this design, voltammetry measurements may be performed using a three-electrodes method, i.e., via a working electrode (WE) (e.g., the second sensor 140/240), a counter electrode (CE), and a reference electrode (RE). A three-electrode system prevents the passage of current through the reference electrode, thereby maintaining its potential during the measurements. The stability of the reference electrode potential results in a more accurate determination of redox potentials which are used for identification of neurotransmitter molecules in FSCV. Circuit simulation results indicate that the current detection range of the prototype front-end circuitry may be between 500 pA to 80 nA, with a resolution of 100 pA or less.

Figure 18A:
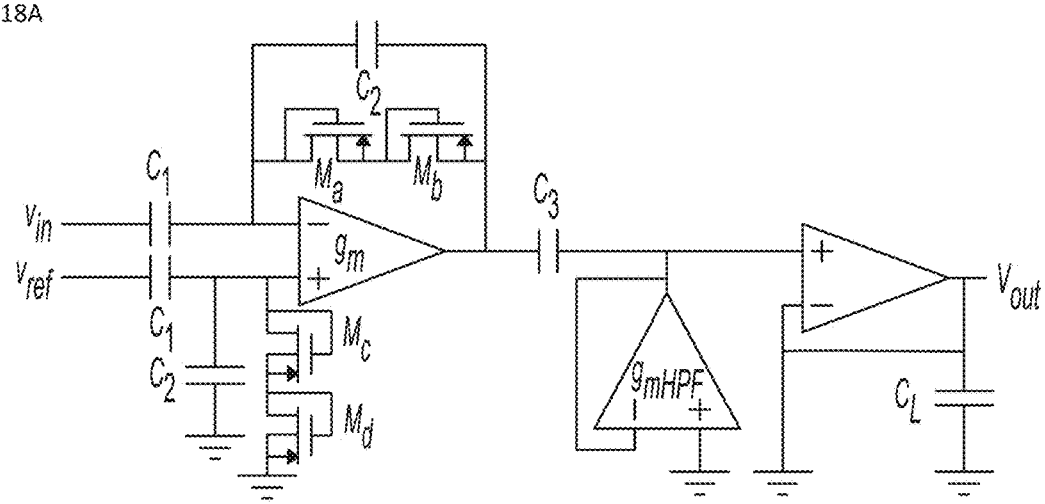
FIGS. 18A and B are schematic circuit diagrams of an action potential signal and field potential signal sensing circuitry, respectively.
Figure 18B:
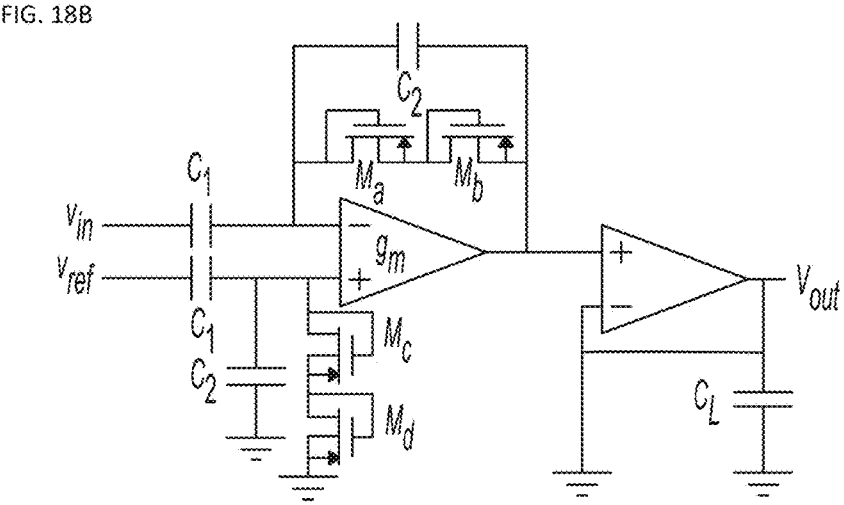

FIGS. 18A and 18B are schematic circuit diagrams of an action potential signal and field potential signal sensing circuitry, respectively. The specifications of action potential signal and field potential signal sensing circuitries may include (i) mid-band gain of 40 dB to 60 dB, (ii) bandpass filter with −3 dB bandwidth from sub-Hz to 1 KHz, and (iii) input referred noise below the background noise of the recoding site (5-10 microVolts). The total power consumption and noise efficiency factor (NEF) may be used as figures of merit for benchmarking the performance of the circuits.

Figure 19:
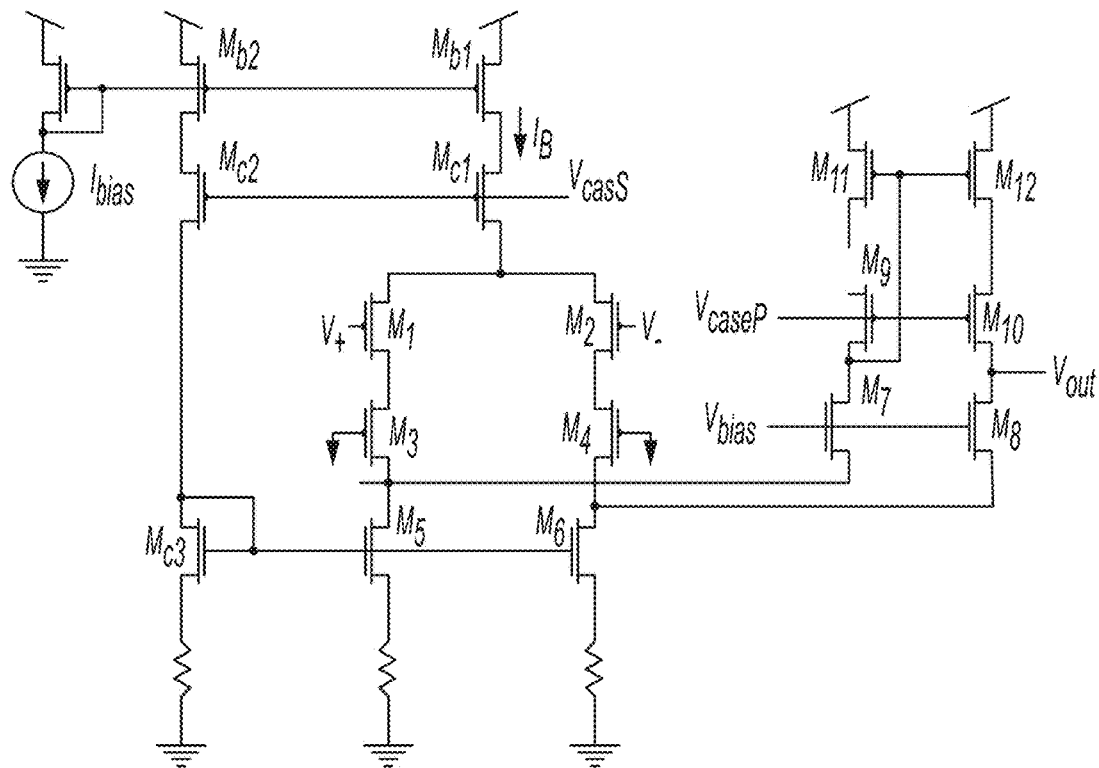
FIG. 19 is a transistor level schematic illustration of an amplifier circuit with source generation for reducing power consumption and input-referred noise of the circuit.

Since extracellular neural signals are very weak, usually from a few tens to hundreds of microVolts, an ultra-low-noise amplifier should be incorporated in a neural recording system before any further signal processing. Desirable properties from an amplifier included in such circuits include: (1) amplification of neural signals in the desired bandwidth for easier signal processing and (2) keeping the equivalent input-referred noise of the amplifier below the background noise of the recording site (5-10 microVolts) so as not to corrupt the electrophysiological signals. Moreover, for in vivo measurements using multi-electrode systems, power consumption should be kept as low as possible to prevent heat dissipation that might damage the nearby neurons. FIG. 19 is a schematic circuit diagram of an energy-efficient neural recording amplifier topology. The amplifier uses a differential input pair to enhance the common-mode rejection rate and to enhance the power supply rejection rate. Large input transistors may be utilized to increase the transconductance of the input pair and reduce the noise.

Figure 20A:
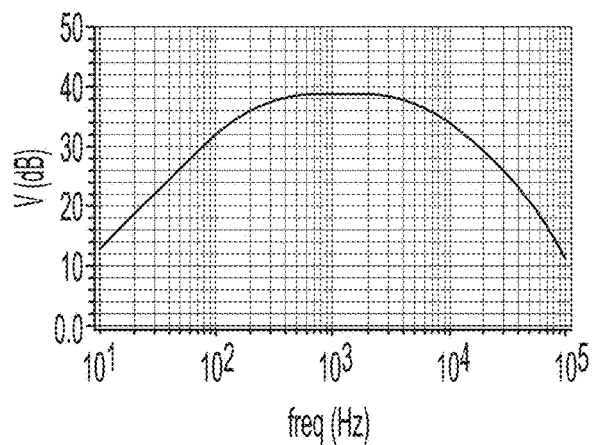
FIG. 20A is a plot of alternating current (AC) response of the action potential.
Figure 20B:
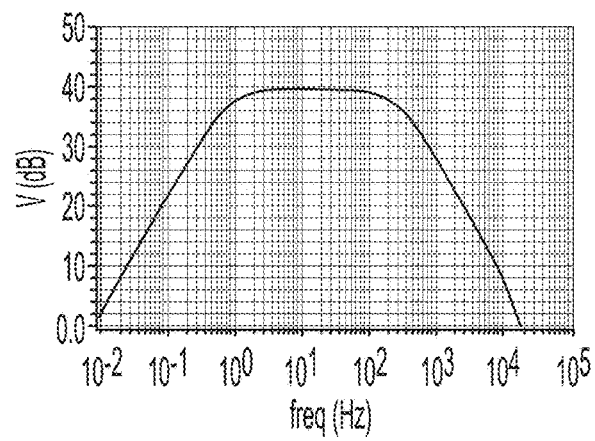
FIG. 20B is a plot of alternating current (AC) response of the field potential detection circuits of FIGS. 18A and B, respectively.

A source-degeneration technique may be utilized to reduce the current in the folded output branch. More specifically, the current in the folded branch is only a small portion of the input differential pair which results in the reduction of the total current consumption of the circuit as well as the total input-referred noise of the amplifier. With reference to FIG. 20A-B, the AC response indicates a 3 -dB bandwidth of 200 Hz-7.5 kHz and gain of about 39 dB for the action potential detection circuit. The AC response plot of the local field potential circuit represents gain of 39.5 dB and a 3-dB bandwidth of 0.3 Hz-300 Hz.

In order to reduce the number of interface signals between the neural recording system and the brain, a global reference current with a start-up circuit that is integrated on the chip may be used. The global reference current may provide an accurate internal reference, which may act as a bias current for the amplifier and for the local bias voltage generation circuit, thus making external voltage or current reference unnecessary. Therefore, the system described herein can start recording once it is powered up. These circuit blocks may be shared between the FSCV and the neural recording circuits.

Sensor Assembly Method of Use

Figure 25:
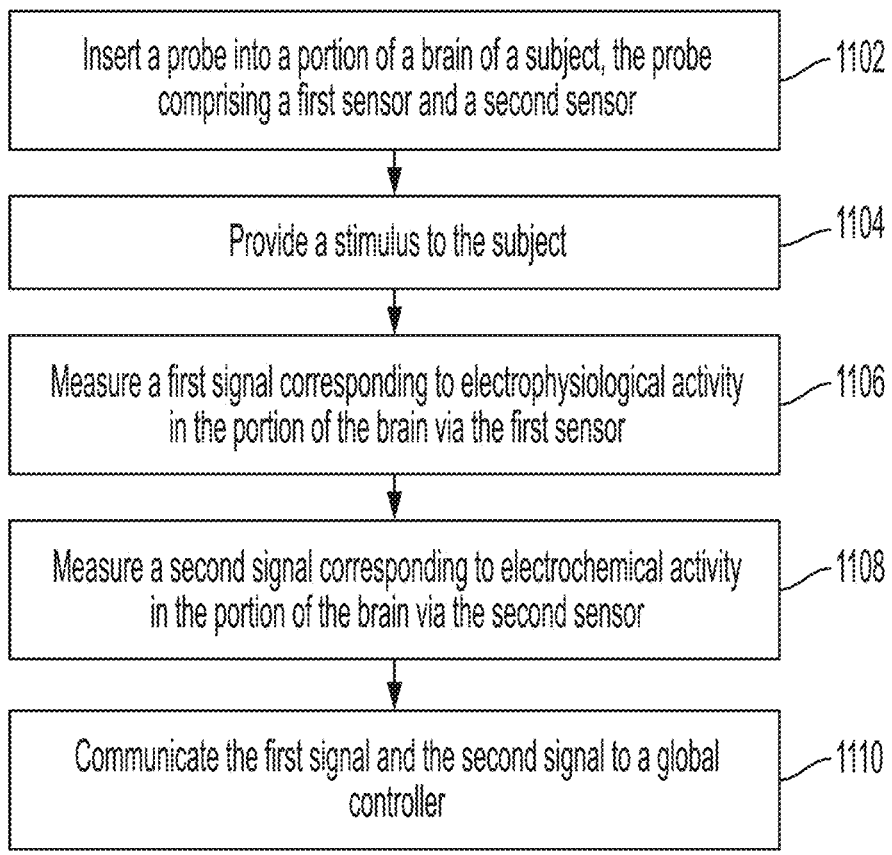
FIG. 25 is a schematic flow diagram of an example method of simultaneously measuring electrophysiological and electrochemical signals in a portion of a brain of a patient.

While the system 100 has been generally described above, FIG. 25 is a schematic flow diagram of an example in vivo measurement method 1100. Specifically, FIG. 25 illustrates a method for simultaneous measurement of electrophysiological activity and chemical changes in a portion of a brain of a subject. The method 1100 includes inserting a probe into a portion of a brain of a subject at 1102. The probe comprises a first sensor configured to measure electrophysiological signals in the portion of the brain and a second sensor configured to measure chemical signals in the portion of the brain. For example, the probe may include the sensor assembly 100/200/700 or any other sensor assembly described herein, which includes the first sensor 120/220/320/720 and the second sensor 140/240/340/440/540/640/740. The portion of the brain may include at least one of a striatum and the frontal cortex, and the chemical responses may correspond to dopamine release in the portion of the brain.

A stimulus is provided to the subject at 1104. The stimulus may include a visual, auditory or tactile stimulus. A first signal corresponding to electrophysiological activity in the portion of the brain is measured via the first sensor at 1106. A second signal corresponding to neurotransmitter release in the portion of the brain is measured via the second sensor at 1108. In some embodiments, a voltammetry scan signal (e.g., having a voltage ramp rate in a range of 0.1 Volts per second to 2,400 Volts per second) is provided to the second sensor (e.g., the second sensor 140/240/340/440/540/640/740) to perform the electrochemical measurement. The FSCV signal includes a dual-slop voltage ramp configured to produce an electrochemical signal in the second sensor. The electrochemical signal may include a background current and an electrochemical current.

The first and second signals are communicated to a global controller 1110. For example, the first signal corresponding to electrophysiological activity and the second signal corresponding to neurotransmitter (e.g., dopamine) concentration are communicated to the global controller (e.g., the global controller 192/692/792). In some embodiments, the first signal and second signal is processed (e.g., by the control circuitry 170/670/770 etc.) before communicating to the global controller. For example, measuring the first signal includes filtering noise from the first signal via a band pass filter, and converting the first signal from an analog to a digital signal, which is provided to the global controller. In some embodiments, measuring the second signal includes subtracting the background current from the electrochemical signal produced by the second sensor. At least a component of the second signal is auto-zeroed, as previously described herein, so as to cancel the voltage offset included in the second signal and reduce low frequency noise. The second signal, which comprises an analog signal, is then converted into a digital signal which is provided to the global controller.

Exemplary Computer System

Figure 26:
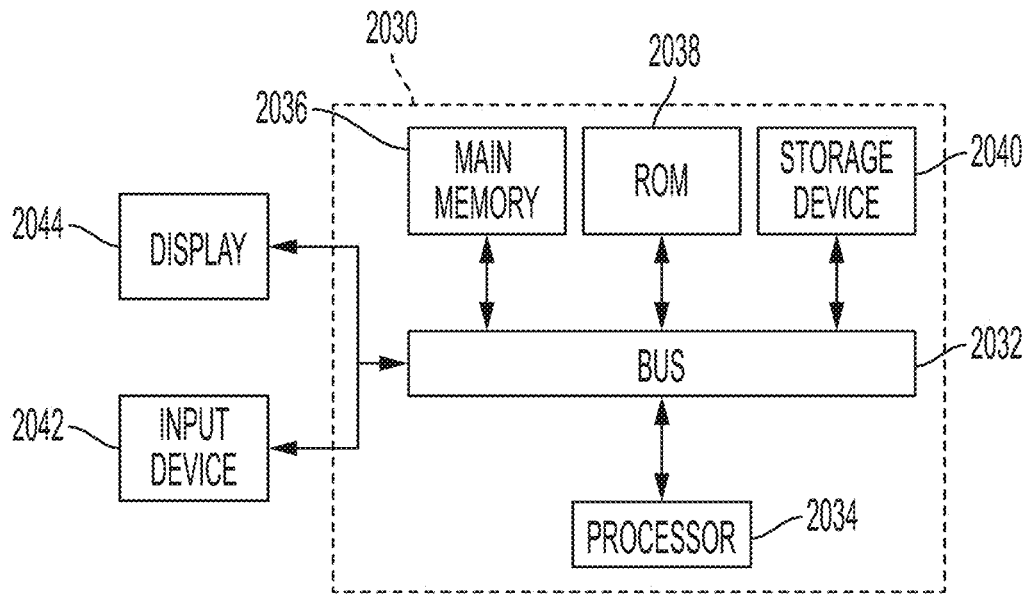
FIG. 26 is a schematic block diagram of one embodiment of a computing device used as the front-end circuitry of FIG.

In some embodiments, the global controller 192/692, the user interface 694, the control circuitry 170/670/770 or any of the controller or control circuitries described herein can comprise a system computer of an apparatus or system which includes a sensor assembly, for example the sensor assembly 100/200/700 or any other sensor assembly described herein. For example, FIG. 26 is a block diagram of a computing device 2030 in accordance with an illustrative implementation. The computing device 2030 can be used to perform any of the methods or the processes described herein, for example the method 1100. The computing device 2030 includes a bus 2032 or other communication component for communicating information. The computing device 2030 can also include one or more processors 2034 or processing circuits coupled to the bus 2032 for processing information.

The computing device 2030 also includes main memory 2036, such as a random access memory (RAM) or other dynamic storage device, coupled to the bus 2032 for storing information, and instructions to be executed by the processor 2034. Main memory 2036 can also be used for storing position information, temporary variables, or other intermediate information during execution of instructions by the processor 2034. The computing device 2030 may further include ROM 2038 or other static storage device coupled to the bus 2032 for storing static information and instructions for the processor 2034. A storage device 2040, such as a solid-state device, magnetic disk or optical disk, is coupled to the bus 2032 for persistently storing information and instructions.

The computing device 2030 may be coupled via the bus 2032 to a display 2044, such as a liquid crystal display, or active matrix display, for displaying information to a user. An input device 2042, such as a keyboard or alphanumeric pad, may be coupled to the bus 2032 for communicating information and command selections to the processor 2034. In another implementation, the input device 2042 has a touch screen display 2044.

According to various implementations, the processes and methods described herein can be implemented by the computing device 2030 in response to the processor 2034 executing an arrangement of instructions contained in main memory 636 (e.g., the operations of the method 1100). Such instructions can be read into main memory 2036 from another non-transitory computer-readable medium, such as the storage device 2040. Execution of the arrangement of instructions contained in main memory 2036 causes the computing device 2030 to perform the illustrative processes described herein. One or more processors in a multi-processing arrangement may also be employed to execute the instructions contained in main memory 2036. In alternative implementations, hard-wired systems may be used in place of or in combination with software instructions to effect illustrated implementations. Thus, implementations are not limited to any specific combination of hardware and software.

Although an example computing device has been described in FIG. 26, implementations described in this specification can be implemented in other types of digital electronic, or in computer software, firmware, or hardware, including the structures disclosed in this specification and their structural equivalents, or in combinations of one or more of them.

Implementations described in this specification can be implemented in digital electronic, or in computer software, firmware, or hardware, including the structures disclosed in this specification and their structural equivalents, or in combinations of one or more of them. The implementations described in this specification can be implemented as one or more computer programs, i.e., one or more circuitries of computer program instructions, encoded on one or more computer storage media for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate components or media (e.g., multiple CDs, disks, or other storage devices). Accordingly, the computer storage medium is both tangible and non-transitory.

The operations described in this specification can be performed by a data processing apparatus on data stored on one or more computer-readable storage devices or received from other sources. The term "data processing apparatus" or "computing device" encompasses all kinds of apparatus, devices, and machines for processing data, including by way of example a programmable processor, a computer, a system on a chip, or multiple ones, or combinations of the foregoing. The apparatus can include special purpose logic, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming languages, including compiled or interpreted languages, declarative or procedural languages, and it can be deployed in any form, including as a stand-alone program or as a circuitry, component, subroutine, object, or other units suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more circuitries, sub-programs, or portions of code). A computer program can be deployed to be executed on one computer, executed on multiple computers that are located at one site, or distributed across multiple sites and interconnected by a communication network.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic.

Definitions

It should be noted that the term "example" as used herein to describe various embodiments is intended to indicate that such embodiments are possible examples, representations, and/or illustrations of possible embodiments (and such term is not intended to connote that such embodiments are necessarily extraordinary or superlative examples).

As used herein, the terms "about" and "approximately" generally mean plus or minus 10% of the stated value. For example, about 0.5 would include 0.45 and 0.55, about 10 would include 9 to 11, about 1000 would include 900 to 1100.

As used herein, the term "micro" refers to having a size in the range of 1 micron to 999 microns inclusive of all ranges and values there between, and term "nano" refers to having a size in the range of 1 nanometer to 999 nanometer.

In the above description, certain terms may be used such as "up," "down," "upper," "lower," "top," "bottom," "upper," "lower," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise.

The terms "coupled," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Additionally, it should be understood that features from one embodiment disclosed herein may be combined with features of other embodiments disclosed herein as one of ordinary skill in the art would understand. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A sensor assembly, comprising:
    a substrate structured to be inserted into a portion of a body of a subject; and
    a potentiometric electrochemical sensor positioned on the substrate, the potentiometric electrochemical sensor comprising a planar multilayer graphene and a field-effect transistor (FET) configured to: receive an activating signal for redox of an analyte included in a bodily fluid present in the portion of the body in contact with a surface of the planar multilayer graphene; and sense an electrochemical signal produced by the redox of the analyte, the electrochemical signal indicative of a concentration of the analyte, wherein the planar multilayer graphene has first and second end portions that are located directly on a surface of an insulator layer, and a middle portion, located laterally adjacent to, and between the first and second end portions, that is entirely spaced apart from, and suspended over, the FET by an air gap which is present entirely through the insulator layer.

2. The sensor assembly of claim 1, wherein the insulator layer is adjacent to a top gate electrode of the FET.

3. The sensor assembly of claim 1, wherein the substrate comprises a silicon-on-insulator (SOI) substrate, and wherein the FET is present in the silicon-on-insulator substrate.

4. The sensor assembly of claim 1, wherein the FET comprises a silicon channel interposed between a top gate dielectric and a bottom gate dielectric.

5. The sensor assembly of claim 4, wherein a thickness of at least one of the top gate dielectric, the bottom gate dielectric and the silicon channel is adjusted to tune an overall sensitivity of the sensor assembly.

6. The sensor assembly of claim 1, wherein the multilayer graphene is configured to be polarized at a constant potential so as to cause the redox reaction with the analyte.

7. The sensor assembly of claim 6, wherein the constant potential is applied with respect to a voltage applied to the source terminal of the FET such that the sensor assembly does not include a reference electrode.

8. The sensor assembly of claim 7, wherein the redox reaction of the analyte generates excess electrons that alter electrical characteristics of the FET.

9. The sensor assembly of claim 1, further comprising:
a front-end circuitry, comprising at least an amplifier, and an analog-to-digital conversion (ADC) circuitry, wherein the FET is connected to the front-end circuit, and wherein the ADC circuitry is configured to amplify and digitize an analog signal generated by the FET into a digital signal.

10. The sensor assembly of claim 1, wherein the substrate contains a plurality of mechanical strength inducing spines positioned therein.

\* \* \* \* \*